(12) United States Patent
Ishii et al.

(10) Patent No.: US 9,924,852 B2
(45) Date of Patent: Mar. 27, 2018

(54) INSERTION APPARATUS

(71) Applicant: OLYMPUS CORPORATION, Tokyo (JP)

(72) Inventors: Hiroo Ishii, Yokohama (JP); Yoshiyuki Tanii, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/235,746

(22) Filed: Aug. 12, 2016

(65) Prior Publication Data

US 2016/0345806 A1 Dec. 1, 2016

Related U.S. Application Data

(63) Continuation of application No. PCT/JP2015/053939, filed on Feb. 13, 2015.

(30) Foreign Application Priority Data

Feb. 13, 2014 (JP) .................................. 2014-025582
Mar. 5, 2014 (JP) .................................. 2014-043109

(51) Int. Cl.
  *A61B 1/00* (2006.01)
  *A61B 1/005* (2006.01)
  (Continued)

(52) U.S. Cl.
  CPC ............ *A61B 1/0008* (2013.01); *A61B 1/005* (2013.01); *A61B 1/0011* (2013.01);
  (Continued)

(58) Field of Classification Search
  CPC .............. A61B 1/00071; A61B 1/0008; A61B 1/00089; A61B 1/00101; A61B 1/0011;
  (Continued)

(56) References Cited

U.S. PATENT DOCUMENTS 5,438,975 A * 8/1995 Miyagi .............. A61B 1/00071
  600/109
5,876,329 A   3/1999 Harhen
  (Continued)

FOREIGN PATENT DOCUMENTS

CN  103533879 A  1/2014
CN  104545775 A  4/2015
  (Continued)

OTHER PUBLICATIONS

International Search Report, PCT/JP2015/053939, dated Apr. 28, 2015.
  (Continued)

*Primary Examiner* — Ryan Henderson
(74) *Attorney, Agent, or Firm* — Scully, Scott, Murphy & Presser, P.C.

(57) ABSTRACT

An insertion apparatus includes a distal end member formed at a distal end portion of an insertion section inserted into a subject, a cylindrical member disposed in the distal end member, and an annular coupling ring into which the distal end member is inserted, a projecting section of the cylindrical member being pinched between the coupling ring and the distal end member.

1 Claim, 17 Drawing Sheets

(51) Int. Cl.
*A61B 1/06* (2006.01)
*A61B 1/07* (2006.01)
*A61B 1/05* (2006.01)
*G02B 23/24* (2006.01)

(52) U.S. Cl.
CPC ........ *A61B 1/0055* (2013.01); *A61B 1/00071* (2013.01); *A61B 1/00091* (2013.01); *A61B 1/00096* (2013.01); *A61B 1/00101* (2013.01); *A61B 1/00112* (2013.01); *A61B 1/00128* (2013.01); *A61B 1/051* (2013.01); *A61B 1/06* (2013.01); *A61B 1/0676* (2013.01); *A61B 1/0684* (2013.01); *G02B 23/243* (2013.01); *G02B 23/2461* (2013.01)

(58) Field of Classification Search
CPC . A61B 1/00135; A61B 1/00142; A61B 1/005; A61B 1/0051; A61B 1/0052; A61B 1/0053; A61B 1/0055; A61B 1/0056; A61B 1/0057; A61B 1/008; A61B 1/00137; A61B 1/0014; A61B 1/00163; A61B 1/00165; A61B 1/00167; A61B 1/0017; A61B 1/00172; A61B 1/00174; A61B 1/00177; A61B 1/00179; A61B 1/00181; A61B 1/00183; A61B 1/07; A61B 1/00186; A61B 1/00189; A61B 1/0019; A61B 1/00192; A61B 1/002; A61B 1/0058; A61B 1/01; A61B 1/04; A61B 1/05; A61B 1/06; A61B 2017/003; A61B 2017/00305; A61B 2017/00309; A61B 2017/00314; A61B 2017/00318; A61B 2017/00323; A61B 2017/00327; A61B 2017/00331
See application file for complete search history.

(56) References Cited

U.S. PATENT DOCUMENTS

| | | |
|---|---|---|
| 6,447,445 B1 | 9/2002 | Hirano |
| 2014/0148644 A1* | 5/2014 | Levi .................. A61B 1/00089 600/104 |

FOREIGN PATENT DOCUMENTS

| | | |
|---|---|---|
| JP | 04-259436 A | 9/1992 |
| JP | 05-154101 A | 6/1993 |
| JP | 08-136829 A | 5/1996 |
| JP | 2001-083436 A | 3/2001 |

OTHER PUBLICATIONS

Japanese Office Action, Japanese Patent Application No. 2015-529946, dated Jan. 26, 2016.

* cited by examiner

INSERTION APPARATUS

CROSS REFERENCE TO RELATED APPLICATIONS

This application is a continuation application of PCT/JP2015/053939 filed on Feb. 13, 2015 and claims benefit of Japanese Applications No. 2014-025582 filed in Japan on Feb. 13, 2014, and No. 2014-043109 filed in Japan on Mar. 5, 2014, the entire contents of each of which are incorporated herein by their reference.

BACKGROUND OF INVENTION

1. Field of the Invention

The present invention relates to an insertion apparatus including an insertion section inserted into a lumen inside, a pipe inside, or the like.

2. Description of the Related Art

In recent years, in a medical field, an industrial field, and the like, an electronic endoscope (hereinafter referred to as endoscope) incorporating an image pickup unit including solid-state image pickup device such as a CCD as an observation optical system at a distal end portion of an elongated insertion section has been used.

In some endoscopes, at a distal end portion of the endoscope, besides an observation unit, an illumination optical unit configuring an illumination optical system, a channel unit configuring a treatment instrument channel, a nozzle unit for air/water feeding, and the like are provided.

In an endoscope in which a bending section is provided in an elongated flexible insertion section, when observation, inspection, and the like are performed, the insertion section is inserted into a lumen of a living organism or into an engine, a pipe, or the like. In an endoscope in which a channel tube is provided along a longitudinal axis in an elongated insertion section, various kinds of medical treatment and the like can be performed by a treatment instrument led into a body via the channel tube and repairing and the like can be performed by a tool led into the pipe via the channel tube.

For example, Japanese Patent Application Laid-Open Publication No. H5-154101 discloses a slip-off preventing screw for fixing a channel distal end member to a distal end constituent member, a slip-off preventing screw for fixing a lens frame cover to the distal end constituent member, and a slip-off preventing screw for detachably attaching a unit main body of a lamp unit to the distal end constituent member.

Japanese Patent Application Laid-Open Publication No. H8-136829 discloses a screw for image pickup unit fixing for fixing a lens frame to a distal end constituent member, a pointed tip screw for fixing a nozzle to the distal end constituent member, and a screw for fixing a light guide to the distal end constituent member.

The endoscope described in the two Japanese publications above has a structure in which distal end side portions of endoscope internal components are fixed to the distal end constituent member by the screws. In order to realize a reduction in a diameter of the insertion section and firm fixing of the endoscope internal components to the distal end constituent member, the distal end constituent member is configured by a metal member and the number of threads is set to a minimum.

SUMMARY OF THE INVENTION

An insertion apparatus according to an aspect of the present invention includes: a distal end member formed at a distal end portion of an insertion section inserted into a subject; a cylindrical member inserted in the distal end member toward a distal end direction of the insertion section, and including a projecting section whose distal end side is abutted against an abutting surface formed on the distal end member, wherein the projecting section is exposed to an outer circumference of the distal end member, with the projecting section abutted against the abutting surface; and an annular coupling ring that configures a distal end portion of a bendable bending section coupled to the distal end member and includes a contact surface which is brought into contact with a proximal end side of the projecting section of the cylindrical member, the coupling ring fixing the cylindrical member by pinching the projecting section between the contract surface and the abutting surface.

DETAILED DESCRIPTION OF THE PREFERRED EMBODIMENTS

Figure 1:
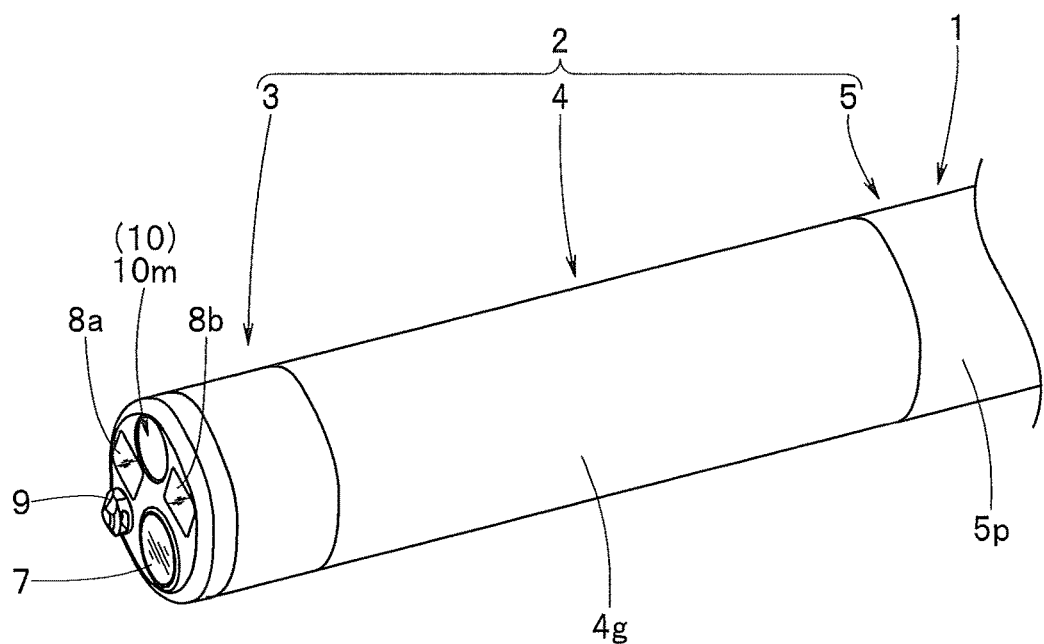
FIG. 1 is a diagram for explaining a configuration of an insertion section of an endoscope.

An embodiment of the present invention is explained below with reference to the drawings.

Note that, in the respective drawings used in the following explanation, scales are sometimes varied for each of components to show the respective components in recognizable sizes on the drawings. The present invention is not limited to only the numbers of the components, shapes of the components, ratios of sizes of the components, and relative positional relations of the respective components described in the drawings.

In recent years, endoscopes are used in a medical field, an industrial field, and the like. As the endoscopes, there are a type in which an elongated insertion section is rigid and a type in which an elongated insertion section is flexible. The endoscope including the flexible elongated insertion section is used as an insertion apparatus.

An insertion section of an endoscope is inserted into a lumen of a living organism or into an engine, a pipe of a plant, or the like and used for observation, inspection, and the like. In general, the endoscope including the flexible elongated insertion section includes a bending section on a distal end side of the insertion section.

A treatment instrument channel is inserted through the insertion section of the endoscope along an insertion section longitudinal axis.

In an endoscope for medical use provided with the treatment instrument channel, a treatment instrument is led into a body via the treatment instrument insert-through channel. On the other hand, in an endoscope for industrial use provided with an insert-through channel, a tool is led in via the insert-through channel.

As shown in FIG. 1, an insertion section 2 included in an endoscope 1 functioning as an insertion apparatus as shown in FIG. 1 is configured by concatenating a distal end portion 3, a bending section 4, and a flexible tube section 5 in order from a distal end side. The bending section 4 is capable of bending, for example, upward, downward, left, and right directions. The flexible tube section 5 has flexibility.

An observation lens 7, a plurality of illumination lenses 8a and 8b, and an air/water feeding nozzle 9 are provided on a distal end face of a distal end cover 6 configuring the distal end portion 3. The observation lens 7 configures an observation optical system. The plurality of illumination lenses 8a and 8b configure an illumination optical system.

An opening 10m of a treatment instrument channel 10, from which the treatment instrument is led out, is formed on the distal end face.

Reference sign 4g denotes a bending tube. The bending tube 4g configures a part of an outermost layer of the distal end portion 3 and an outermost layer of the bending section 4. Reference sign 5p denotes, for example, a resin layer. The resin layer 5p configures an outermost layer of the flexible tube section 5.

A configuration on a distal end side of the insertion section 2 is explained with reference to FIG. 2 to FIG. 9.

Figure 2:
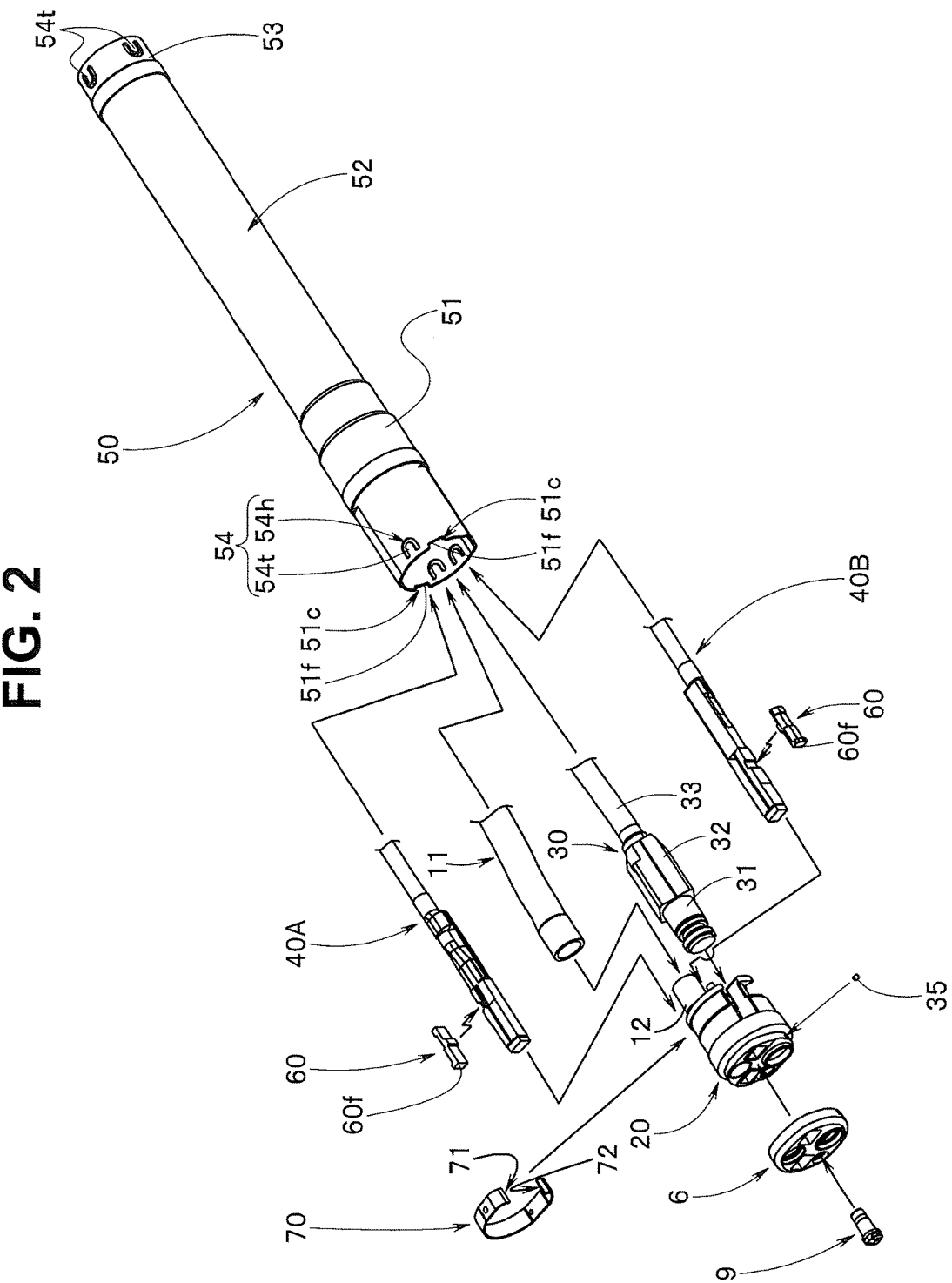
FIG. 2 is an exploded perspective view for explaining a configuration on a distal end side of the endoscope insertion section.

The distal end side of the insertion section 2 mainly includes the distal end cover denoted by reference numeral 6, the air/water feeding nozzle denoted by reference numeral 9, a channel tube denoted by reference numeral 11, a distal-end rigid portion, which is a distal end member, denoted by reference numeral 20, an observation optical unit denoted by reference numeral 30, illumination optical units denoted by reference signs 40A and 40B, a bending section set denoted by reference numeral 50, connecting pieces denoted by reference numeral 60, and a ring member, which is a locking member, denoted by reference numeral 70 in FIG. 2 and the bending tube (not shown in FIG. 2) 4g.

The channel tube 11, the observation optical unit 30, the illumination optical units 40A and 40B, and the like are cylindrical members and are so-called endoscope internal components.

Figure 3:
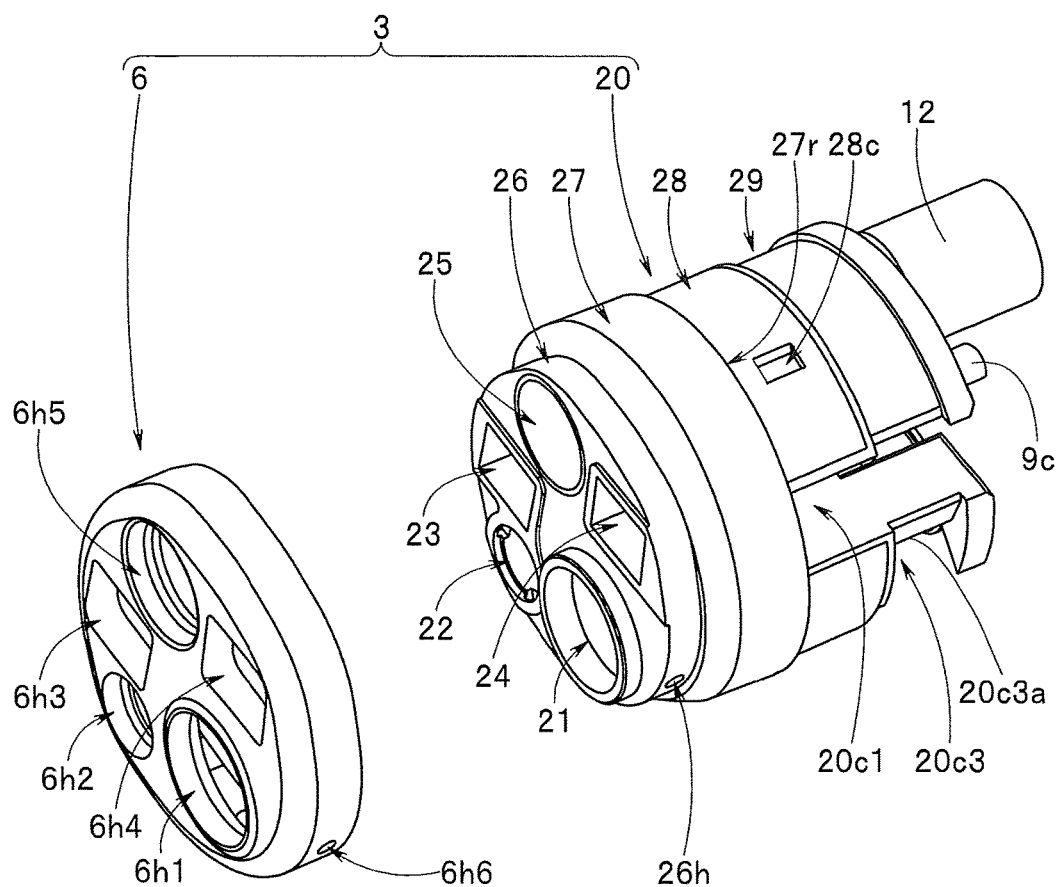
FIG. 3 is a diagram for explaining a distal end cover and a distal-end rigid portion configuring a distal end portion.

As shown in FIG. 2 and FIG. 3, the distal end portion 3 is mainly configured by the distal end cover 6 and the distal-end rigid portion 20.

As an example, the distal end cover 6 is cylindrical and is made of, for example, resin. In the distal end cover 6, a through-hole for observation optical system 6h1, a through-hole for nozzle 6h2, a first through-hole for illumination optical system 6h3, a second through-hole for illumination optical system 6h4, and a through-hole for channel 6h5 are provided.

The observation lens 7 is fixed to the through-hole for observation optical system 6h1 while keeping water tightness. The air/water feeding nozzle 9 is fixed to the through-hole for nozzle 6h2 while keeping water tightness. The first illumination lens 8a is fixed to the first through-hole for illumination optical system 6h3 while keeping water tightness. The second illumination lens 8b is fixed to the second through-hole for illumination optical system 6h4 while keeping water tightness.

Note that a center axis (not shown in the figure) of the through-hole for observation optical system 6h1, a center axis (not shown in the figure) of the through-hole for nozzle 6h2, a center axis (not shown in the figure) of the first through-hole for illumination optical system 6h3, a center axis (not shown in the figure) of the second through-hole for illumination optical system 6h4, and a center axis (not shown in the figure) of the through-hole for channel 6h5 are respectively parallel to a center axis (not shown in the figure) of the distal end cover 6.

In the present embodiment, sectional shapes of the through-hole for observation optical system 6h1, the through-hole for nozzle 6h2, and the through-hole for channel 6h5 are shown as circular shapes. On the other hand, a sectional shape of the first through-hole for illumination optical system 6h3 and the second through-hole for illumination optical system 6h4 is shown as a rectangular shape. However, the sectional shapes of the respective through-holes are not limited to these shapes and are set as appropriate according to shapes of members disposed in the through-holes.

The distal-end rigid portion 20 is formed in a columnar shape and is made of, for example, rigid resin. In the distal-end rigid portion 20, for example, a first retaining hole 21, a second retaining hole 22, a third retaining hole 23, a fourth retaining hole 24, and a channel hole 25 are provided. The plurality of holes 21, 22, 23, 24, and 25 are through-holes. Predetermined internal components are retained in the retaining holes 21, 22, 23, and 24.

Note that the distal-end rigid portion 20 is not limited to be made of resin as long as the distal-end rigid portion 20 is a rigid member. The distal-end rigid portion 20 may be made of metal such as stainless steel or made of ceramic or the like.

A center axis (not shown in the figure) of the first retaining hole 21, a center axis (not shown in the figure) of the second retaining hole 22, a center axis (not shown in the figure) of the third retaining hole 23, a center axis (not shown in the figure) of the fourth retaining hole 24, and a center axis (not shown in the figure) of the channel hole 25 are respectively parallel to a center axis (not shown in the figure) of the distal-end rigid portion 20.

The first retaining hole 21 is a through-hole for observation optical system. A frame section 31 of the observation optical unit 30 is disposed in the hole 21.

The second retaining hole 22 is a through-hole for nozzle. A nozzle main body section 9b of the air/water feeding nozzle 9 and a distal end side portion of an air/water feeding pipe sleeve 9c are disposed in the hole 22. A proximal end side portion of the air/water feeding pipe sleeve 9c projects from a proximal end face side of the distal-end rigid portion 20. A distal end portion of an air/water feeding tube (not shown in the figure) is fixed to the projecting air/water feeding pipe sleeve 9c.

The third retaining hole 23 is a first through-hole for illumination optical system. A distal end portion of the first illumination optical unit 40A is disposed in the hole 23.

The fourth retaining hole 24 is a second through-hole for illumination optical system. A distal end portion of the second illumination optical unit 40B is disposed in the hole 24.

The channel hole 25 is a through-hole for treatment instrument channel. A distal end side portion of a pipe sleeve for channel 12 is disposed in the hole 25. A proximal end side portion of the pipe sleeve for channel 12 projects from a proximal end face side of the distal-end rigid portion 20. A distal end portion of the channel tube 11 is fixed to the projecting pipe sleeve for channel 12.

In the present embodiment, sectional shapes of the first retaining hole 21, the second retaining hole 22, and the channel hole 25 are shown as circular shape. On the other hand, a sectional shape of the third retaining hole 23 and the fourth retaining hole 24 is shown as a rectangular shape. However, the sectional shapes of the respective through-holes are not limited to these shapes and are set as appropriate according to shapes of members disposed in the through-holes.

On an outer circumferential surface of the distal-end rigid portion 20, a distal-end-cover fixing surface 26, a rigid portion flange 27, a coupling-ring disposing surface 28, and a groove for ring setting 29 are provided in order from a distal end side.

On the distal-end-cover fixing surface 26, the distal end cover 6 is externally fit and disposed in a predetermined state. The externally-fit and disposed distal end cover 6 is integrally fixed to the distal-end rigid portion 20. In this fixed state, the center axis of the through-hole for observation optical system 6h1 and the center axis of the first retaining hole 21 are coaxially disposed, the center axis of the through-hole for nozzle 6h2 and the center axis of the second retaining hole 22 are coaxially disposed, the center axis of the first through-hole for illumination optical system 6h3 and the center axis of the third retaining hole 23 are coaxially disposed, the center axis of the second through-hole for illumination optical system 6h4 and the center axis of the fourth retaining hole 24 are coaxially disposed, and the center axis of the through-hole for channel 6h5 and the center axis of the channel hole 25 are coaxially disposed.

Note that a communication hole 26h connecting an outside and an inside of the first retaining hole 21 is formed on the distal-end-cover fixing surface 26. A locking pin 35 is inserted through and disposed in the communication hole 26h. Reference sign 6h6 denotes a release hole provided in the distal end cover 6. The release hole 6h6 connects the outside and an inside of the through-hole for observation optical system 6h1. The locking pin 35 is inserted through and disposed in the release hole 6h6.

The rigid portion flange 27 includes one end face and the other end face orthogonal to the center axis of the distal-end rigid portion 20. A proximal end face of the distal end cover 6 is set in contact with and disposed on the one end face located on a distal end side of the rigid portion flange 27. On the other hand, the other end face located on a proximal end side of the rigid portion flange 27 is a flange abutting surface 27r. Distal end faces 60f explained below of the connecting pieces 60 are in contact with the flange abutting surface 27r. In a state in which the distal end faces 60f are in contact with the flange abutting surface 27r, an outer surface of the rigid portion flange 27 and an outer surface of a distal end side flange 63 configure substantially the same surface.

A distal-end bending die 51 configuring the bending section set 50 is externally fit and disposed on the coupling-ring disposing surface 28. That is, the distal-end rigid portion 20 is inserted into and disposed in an inside of the distal-end bending die 51. A locking section 28*c* is provided on the coupling-ring disposing surface 28. The locking section 28*c* is a recessed section in which a tongue-like section 54*t* provided in the distal-end bending die 51 is disposed. A plurality of locking sections 28*c* are provided to match tongue piece sections 54.

The groove for ring setting 29 is a concave-shape circumferential groove formed in a middle of the coupling-ring disposing surface 28. The ring member 70 is engaged and disposed in the groove for ring setting 29.

A first cutout section denoted by reference sign 20*c*1, a not-shown second cutout section, and a third cutout section denoted by reference sign 20*c*3 are provided on an outer circumferential surface of the distal-end rigid portion 20.

The first cutout section 20*c*1 forms a housing recessed section having an opening for exposing a part of the fourth retaining hole 24 to the outside. The opening of the housing recessed section formed by the first cutout section 20*c*1 is elongated along the axial direction at predetermined width and is provided in a predetermined position of the coupling-ring disposing surface 28, which is a part of the outer circumferential surface of the distal-end rigid portion 20. The connecting piece 60 provided in the second illumination optical unit 40B housed in the fourth retaining hole 24 is disposed in the first cutout section 20*c*1, which is a housing recessed section.

Like the first cutout section 20*c*1, the second cutout section forms a housing recessed section in which the connecting piece 60 is disposed. The second cutout section exposes a part of the third retaining hole 23, in which the first illumination optical unit 40A is disposed, to the outside.

The third cutout section 20*c*3 forms a housing section in which an image-pickup-section main body 32 of the observation optical unit 30 is disposed. One side end face 20*c*3*a* of the third cutout section 20*c*3 functions as one end side attaching section. The one side end face 20*c*3*a* is formed such that a first claw section 71 of the ring member 70 is hooked and disposed thereon.

Note that the other side end face not shown in the figure of the third cutout section 20*c*3 functions as the other end side attaching section. The other end side attaching section is formed such that a second claw section 72 provided in the ring member 70 is hooked and disposed thereon.

Figure 4:
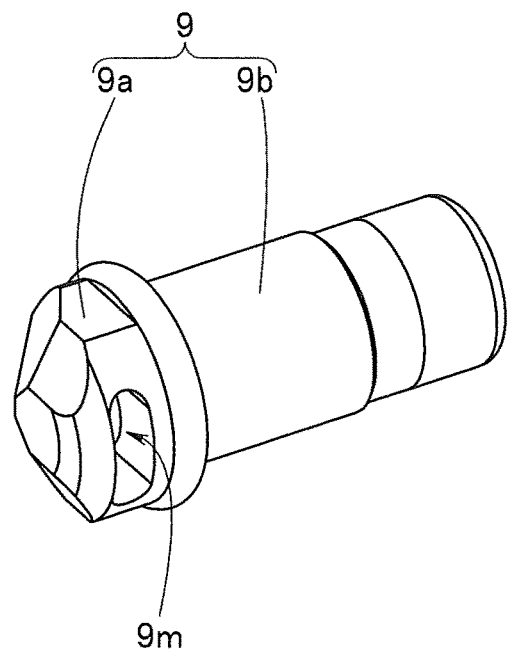
FIG. 4 is a diagram for explaining an air/water feeding nozzle.

As shown in FIG. 4, the air/water feeding nozzle 9 includes a nozzle section 9*a* and the nozzle main body section 9*b*. A fluid ejecting port 9*m* is provided in the nozzle section 9*a*. The nozzle main body section 9*b* is housed and disposed in the through-hole for nozzle 6*h*2 and the second retaining hole 22 and integrally fixed by, for example, bonding.

Figure 5:
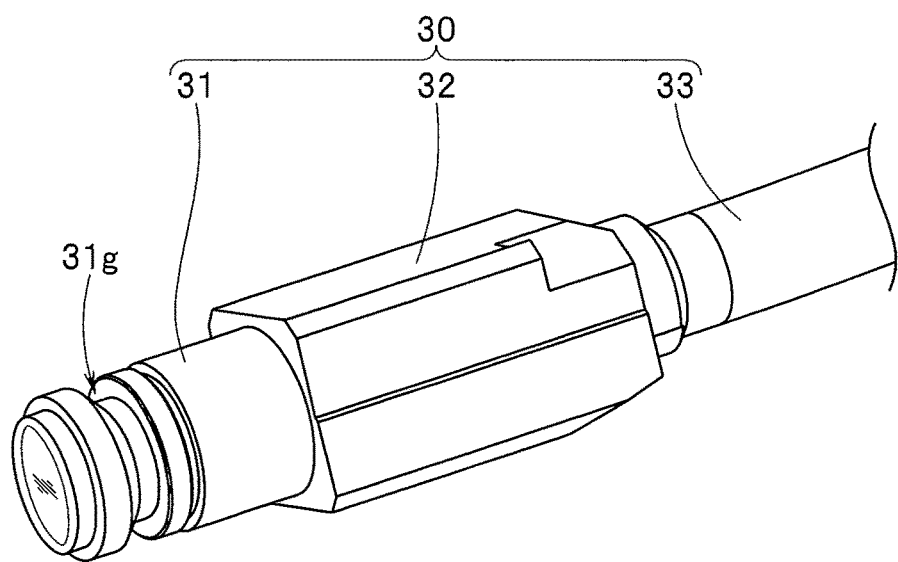
FIG. 5 is a diagram for explaining an observation optical unit.

As shown in FIG. 2 and FIG. 5, in the observation optical unit 30, the frame section 31, the image-pickup-section main body 32, and a signal cable 33 are concatenated in order from a distal end side.

The frame section 31 is formed in a tubular shape. An optical lens (not shown in the figure) and the like are disposed in an inner hole. The frame section 31 is housed in the first retaining hole 21 and the through-hole for observation optical system 6*h*1. A circumferential groove for positioning 31*g* is provided in a predetermined position of the frame section 31. A distal end side portion of the locking pin 35 is disposed in the circumferential groove for positioning 31*g*.

The image-pickup-section main body 32 is formed in a substantially rectangular parallelepiped shape. In the image-pickup-section main body 32, an image pickup device (not shown in the figure) such as a CCD, a substrate (not shown in the figure) mounted with electronic components (not shown in the figure), and the like are disposed. The image-pickup-section main body 32 is housed in the third cutout section 20*c*3.

The signal cable 33 is configured by inserting through a plurality of signal lines. Distal ends of the plurality of signal lines are connected to a contact section provided on the substrate. The signal cable 33 is inserted through the bending section 4 including the bending section set 50 and through the flexible tube section 5 and extended to a proximal end side of the insertion section 2.

Figure 6:
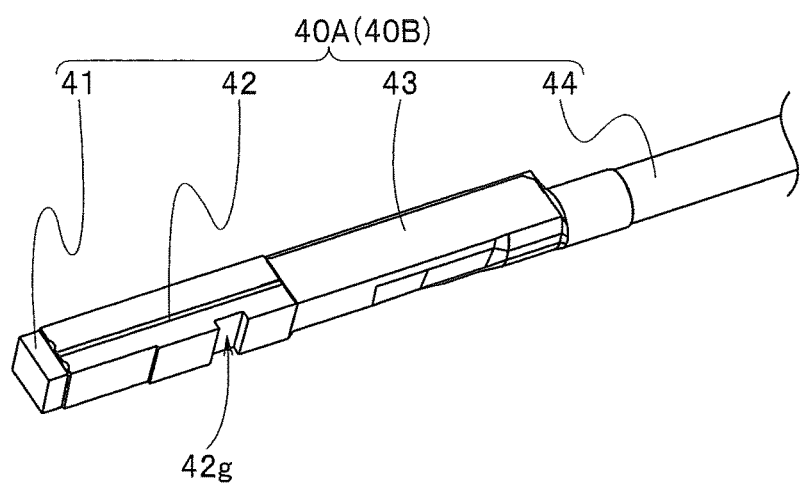
FIG. 6 is a diagram for explaining an illumination optical unit.
Figure 7:
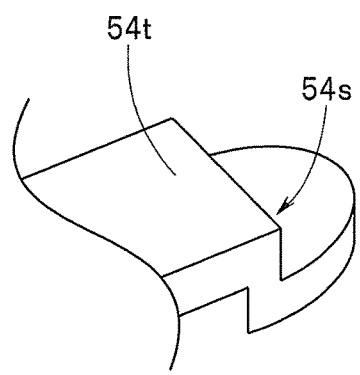
FIG. 7 is a diagram for explaining a stepped tongue piece, which is a configuration example of a tongue-like section configuring a tongue piece section.

As shown in FIG. 2 and FIG. 6, the first illumination optical unit 40A includes an illuminating section 41, a retaining-hole disposing section 42, a coupling section 43, and an insertion-section extending section 44 and is configured. Note that a configuration of the second illumination optical unit 40B is the same as the configuration of the first illumination optical unit 40A. Therefore, explanation of the configuration of the second illumination optical unit 40B is omitted.

The illuminating section 41 is an LED illuminating section having a rectangular shape. The illuminating section 41 is configured by disposing, for example, a plurality of LEDs. The illuminating section 41 is disposed in the first through-hole for illumination optical system 6*h*3 and the second through-hole for illumination optical system 6*h*4, the sectional shape of which is the rectangular shape.

The retaining-hole disposing section 42 is disposed in the third retaining hole 23 and the fourth retaining hole 24. The retaining-hole disposing section 42 is formed to match the shape of the retaining holes 23 and 24. A connecting-piece engaging groove 42*g* is formed in a predetermined part of the retaining-hole disposing section 42. An intermediate flange (see reference numeral 65 in FIG. 8) provided in the connecting piece 60 is engaged and disposed in the connecting-piece engaging groove 42*g*.

A substrate and a plurality of signal lines are disposed in the retaining-hole disposing section 42.

An end portion of the substrate is disposed in the coupling section 43. The plurality of signal lines extending from the substrate are disposed in the coupling section 43. The plurality of signal lines are collectively inserted through the insertion-section extending section 44.

Note that, in the above explanation, the illuminating section 41 is the LED illuminating section. However, the illuminating section 41 may be a distal end portion of a light guide fiber bundle. In that case, the distal end portion of the light guide fiber bundle is formed in a rectangular shape to match the rectangular shape of the first through-hole for illumination optical system 6*h*3 and the second through-hole for illumination optical system 6*h*4.

As shown in FIG. 2, the bending section set 50 is configured to turnably couple the distal-end bending die 51, an intermediate bending die set 52, and a proximal-end bending die 53, which are annularly formed in order from a distal end side, and bend in upward, downward, left, and right directions. The intermediate bending die set 52 is configured to turnably couple a plurality of intermediate bending dies one another and bend in the upward, downward, left, and right directions. In FIG. 2, a plurality of concatenated intermediate bending dies are shown as one collected bending die group rather than being shown one by one.

A recessed section 51*c* surrounding the distal end side flange 63 is provided in the distal-end bending die 51. A bottom surface of the recessed section 51*c* is a flange contact surface 51*f* that is in contact with a coupling-ring contact surface (reference numeral 63*f* in FIG. 8) explained below of the distal end side flange 63.

The distal-end bending die 51 is a coupling ring disposed on a proximal end side of the distal-end rigid portion 20 on the distal end side of the insertion section 2. The distal-end bending die 51 is coupled and fixed to the distal-end rigid portion 20 and configures a distal end portion of the bending section 4. For example, three tongue piece sections 54 are provided in a circumferential direction in the distal-end bending die 51. The tongue piece section 54 includes a cutout hole 54*h* and the tongue-like section 54*t* having elasticity. In the present embodiment, the tongue-like section 54*t* is a stepped tongue piece including a step section 54*s* shown in FIG. 7 at an end portion.

The three tongue piece sections 54 are provided in the circumferential direction at equal intervals or predetermined intervals.

The proximal-end bending die 53 is also a coupling ring. That is, in the proximal-end bending die 53, for example, three tongue piece sections 54 are provided in the circumferential direction at equal intervals or predetermined intervals. The proximal-end bending die 53 is disposed in a coupling member (not shown in the figure) fixed to a distal end portion of the flexible tube section 5.

Figure 8:
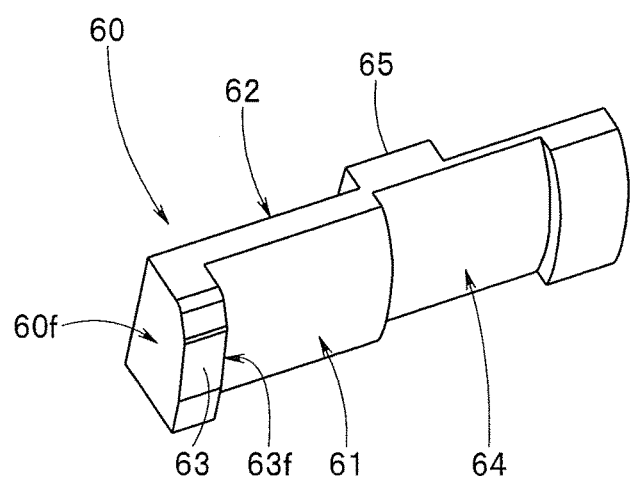
FIG. 8 is a diagram for explaining a connecting piece.

As shown in FIG. 2 and FIG. 8, the connecting pieces 60 are made of metal such as stainless steel. The connecting piece 60 is formed in a substantially rectangular parallelepiped shape. The distal end side flange 63 and a recessed section for ring 64 are provided on a first surface 61, which is one surface. On the other hand, the intermediate flange 65 is provided on a second surface 62, which is the other surface of the connecting piece 60.

The intermediate flange 65 is engaged and disposed respectively in the connecting piece engaging groove 42*g* of the first illumination optical unit 40A and the connecting piece engaging groove 42*g* of the second illumination optical unit 40B. The intermediate flange 65 is a projecting section having a predetermined shape projecting from the second surface 62 by a predetermined amount. The intermediate flange 65 is provided in a position separated from a distal end face of the distal end side flange 63 in the axial direction by a predetermined distance. The distal end face of the distal end side flange 63 is the distal end face 60*f* of the connecting piece 60.

The first illumination optical unit 40A and the connecting piece 60 are configured as separate bodies. However, the first illumination optical unit 40A and the connecting piece 60 may be integrally configured as a cylindrical member.

The distal end side flange 63 is a projecting section having a predetermined shape provided to project from the first surface 61 by a predetermined amount. The distal end face 60*f* of the connecting piece 60 is a contact surface and is in contact with and disposed on the flange abutting surface 27*r* of the rigid portion flange 27 configuring the distal-end rigid portion 20. An opposite surface of the distal end side flange 63 is the coupling-ring contact surface 63*f*. The flange contact surface 51*f* of the distal-end bending die 51 configuring the bending section set 50 is in contact with and disposed on the opposite surface.

The ring member 70 is disposed in the recessed section for ring 64. The first surface 61 of the connecting piece 60 is formed to be substantially flush with an outer surface of the ring member 70 in a state in which the ring member 70 is disposed in the recessed section for ring 64.

Figure 9:
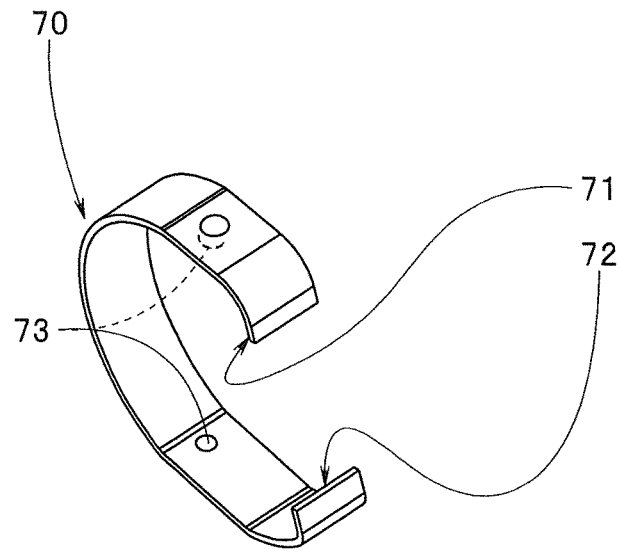
FIG. 9 is a diagram for explaining a ring member.

As shown in FIG. 2 and FIG. 9, the ring member 70 is a spring member made of, for example, phosphor bronze or stainless steel having predetermined elasticity or is made of metal such as a nickel titanium alloy. The ring member 70 is formed in, for example, a C-shape and is formed by bending a belt-like member having a predetermined width dimension. The ring member 70 having the C-shape is mainly housed and disposed in the groove for ring setting 29. A remaining portion of the ring member 70 is disposed in the recessed section for ring 64. Therefore, a bottom surface of the groove for ring setting 29 and a bottom surface of the recessed section for ring 64 form substantially the same circumferential surface.

In a state in which the ring member 70 is housed and disposed in the groove for ring setting 29, the outer surface of the ring member 70 and a surface of the coupling-ring disposing surface 28 form the same outer surface. In other words, in the state in which the ring member 70 is housed and disposed in the groove for ring setting 29, the outer surface of the ring member 70 and the surface of the coupling-ring disposing surface 28 are in a flush state.

The first claw section 71 is provided on one end side of the C-shaped ring member 70. The second claw section 72 is provided on the other end side. On an inner surface side of the ring member 70, a plurality of pressing projecting sections 73 projecting from an inner surface by a predetermined amount are provided on the inner surface side of the ring member 70.

In a state in which the ring member 70 is housed in the groove for ring setting 29, the first claw section 71 is hooked and disposed on the one side end face 20*c*3*a* of the third cutout section 20*c*3 and the second claw section 72 is hooked and disposed on the other side end face of the third cutout section 20*c*3. In this disposition state, the pressing projecting sections 73 are set on a bottom surface of the recessed section for ring 64 of the connecting piece 60.

Note that a sectional shape of the ring member 70 is not limited to the C-shape and may be a circular shape, an inverted C-shape, a polygonal shape, or the like.

An assembly procedure for an endoscope-insertion-section distal end side is explained with reference to FIG. 2 and FIG. 10 to FIG. 14.

In assembling the distal end side of the insertion section 2, an operator prepares the distal end cover 6, the air/water feeding nozzle 9, the channel tube 11, the distal-end rigid portion 20, the observation optical unit 30, the first illumination optical unit 40A, the second illumination optical unit 40B, the bending section set 50, the connecting pieces 60, the ring member 70, the bending tube 4*g*, the air/water feeding tube (not shown in the figure), the locking pin 35, and the like.

Figure 10:
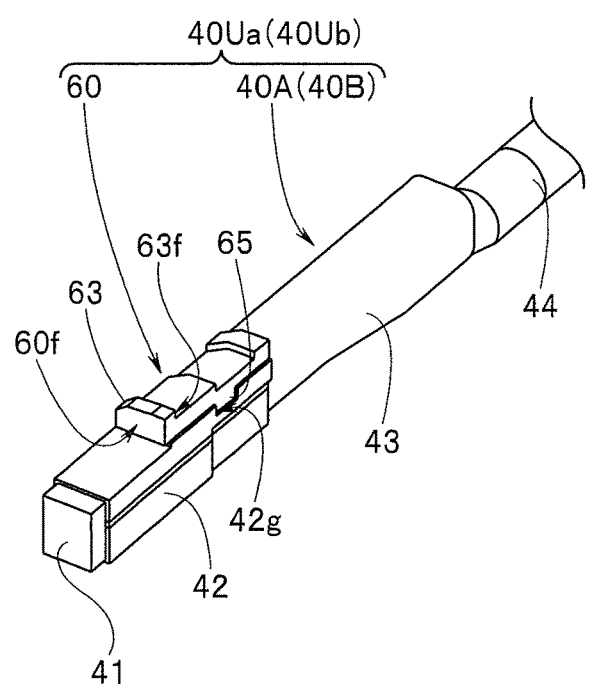
FIG. 10 is a diagram for explaining an assembly procedure for an endoscope-insertion-section distal end side and is a diagram for explaining the illumination optical unit provided with the connecting piece.

Note that the connecting pieces 60 are respectively disposed in the retaining-hole disposing section 42 of the first illumination optical unit 40A and the retaining-hole disposing section 42 of the second illumination optical unit 40B in advance and configured as connecting-piece-integrated illumination units 40Ua and 40Ub shown in FIG. 10.

First, the operator assembles endoscope internal components to the distal-end rigid portion 20. That is, the operator disposes the frame section 31 of the observation optical unit 30 in the first retaining hole 21 formed at the distal-end rigid portion 20 and disposes the image-pickup-section main body 32 in a housing section formed by the third cutout section 20*c*3.

The operator adjusts upper and lower positions of the image pickup device and checks a position of the circumferential groove for positioning 31*g* through the communication hole 26*h*. After checking the position of the circumferential groove for positioning 31*g*, the operator deforms the locking pin 35 and disposes the locking pin 35 in the communication hole 26h and the circumferential groove for positioning 31g and performs positioning in the axial direction.

The operator disposes the first connecting-piece-integrated illumination unit 40Ua in the third retaining hole 23 formed at the distal-end rigid portion 20. Then, the retaining-hole disposing section 42 of the first illumination optical unit 40A is housed in the third retaining hole 23. The connecting piece 60 is exposed to the outside of the distal-end rigid portion 20 from an opening of the first cutout section 20c1. At this point, the distal end face 60f is disposed near the flange abutting surface 27r of the rigid portion flange 27 provided at the distal-end rigid portion 20.

Note that, as explained above, the operator disposes the second connecting-piece-integrated illumination unit 40Ub in the fourth retaining hole 24 formed at the distal-end rigid portion 20. As a result, the distal end face 60f is disposed near the flange abutting surface 27r.

The operator fixes a distal end portion of the air/water feeding tube to the proximal end side portion of the air/water feeding pipe sleeve 9c projecting from the proximal end face side of the distal-end rigid portion 20.

The operator fixes a distal end portion of the channel tube 11 to the proximal end side portion of the pipe sleeve for channel 12 projecting from the proximal end face side of the distal-end rigid portion 20.

Figure 11:
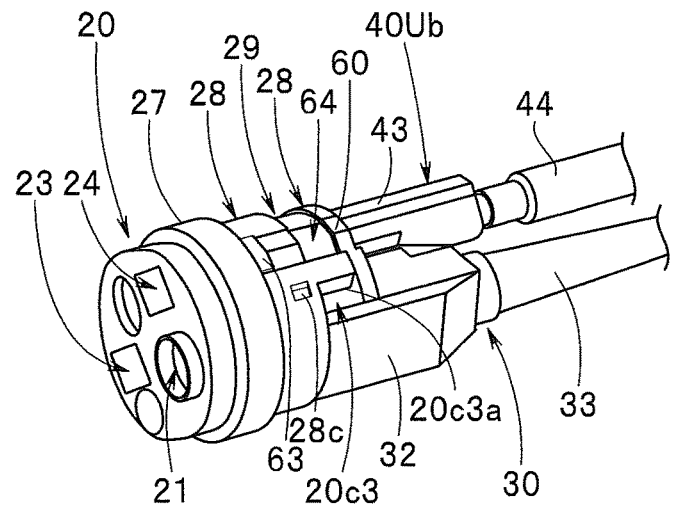
FIG. 11 is a diagram for explaining an assembly procedure for the endoscope insertion section and is a diagram for explaining a state in which endoscope internal components such as the observation optical unit and the illumination optical unit are disposed at the distal-end rigid portion.

As a result, various endoscope internal components are disposed in the distal-end rigid portion 20 as shown in FIG. 11.

Subsequently, the operator shifts to work for assembling the ring member 70 to the distal-end rigid portion 20.

This work is work for mounting the ring member 70 in a circumferential direction groove for ring configured by the groove for ring setting 29 formed in an outer circumference of the distal-end rigid portion 20 and the recessed section for ring 64 of the connecting piece 60 disposed at the distal-end rigid portion 20.

Figure 12:
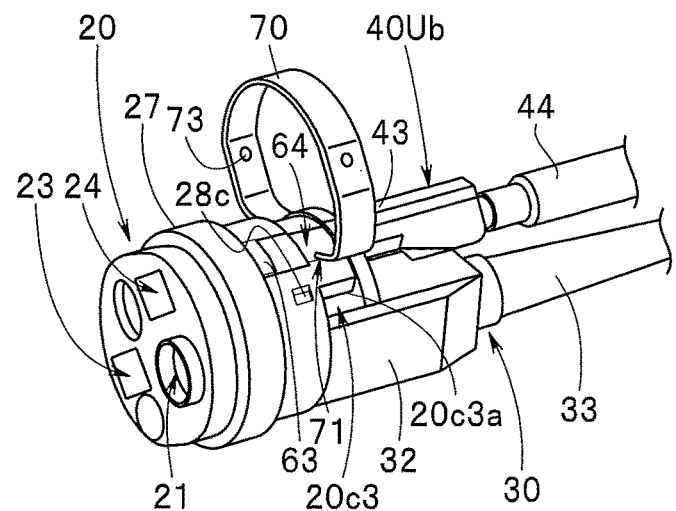
FIG. 12 is a diagram for explaining an assembly procedure for the endoscope insertion section and is a diagram for explaining a process for assembling a ring member to the distal-end rigid portion in which the endoscope internal components are disposed.

The operator abuts the first claw section 71 and the second claw section 72 of the ring member 70 against the coupling-ring disposing surface 28 of the distal-end rigid portion 20 as shown in FIG. 12. Thereafter, the operator hooks, for example, the first claw section 71 to the one side end face 20c3a of the third cutout section 20c3.

Thereafter, the operator elastically deforms the second claw section 72 while moving the second claw section 72 along the coupling-ring disposing surface 28 and hooks the second claw section 72 to the other side end face 20c3b of the third cutout section 20c3. As a result, as shown in 13A, the ring member 70 is assembled in the circumferential groove for ring configured by the groove for ring setting 29 and the recessed section for ring 64.

In this assembled state, the connecting-piece-integrated illumination units 40Ua and 40Ub disposed in the distal-end rigid portion 20 are restricted to a state in which the distal end face 60f is set in contact with the flange abutting surface 27r by the ring member 70 and are retained in a provisionally fixed state in which the connecting-piece-integrated illumination units 40Ua and 40Ub are prevented from coming off in the axial direction from the retaining holes 23 and 24 of the distal-end rigid portion 20.

Subsequently, the operator externally fits and fixes the distal-end bending die 51, which is provided at a most distal end of the bending section set 50 provided at the distal end portion of the flexible tube section 5, to the coupling-ring disposing surface 28.

Figure 13A:
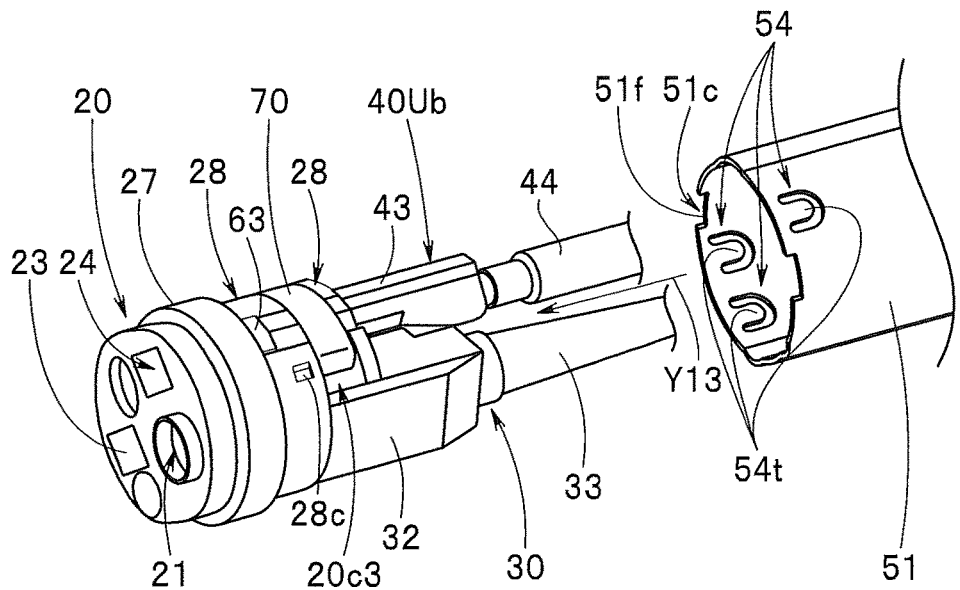
FIG. 13A is a diagram for explaining an assembly procedure for the endoscope insertion section and is a diagram for explaining a step for assembling a distal-end bending die 51 to the distal-end rigid portion in a state in which the endoscope internal components disposed at the distal-end rigid portion are provisionally retained by the ring member.

More specifically, the operator moves the distal-end bending die 51 as indicated by an arrow Y13 in FIG. 13A and disposes a distal end side inner circumferential surface of the bending die 51 on the coupling-ring disposing surface 28 provided on the proximal end side of the distal-end rigid portion 20. Then, the operator moves the distal-end bending die 51 in the axial direction toward the rigid portion flange 27.

By moving the distal-end bending die 51 toward the rigid portion flange 27, the tongue-like section 54t of the stepped tongue piece is disposed on the coupling-ring disposing surface 28.

Note that, in performing the fixing work, the operator provides, in both of the tongue piece section 54 and the locking section 28c, indicators indicating a position of the tongue piece section 54 and a position of the locking section 28c in advance. As the indicators, slits, mark-off lines parallel to the center axes, or the like may be provided.

Thereafter, the operator moves the distal-end bending die 51 toward the rigid portion flange 27 resisting an elastic force of the tongue-like section 54t.

Then, the tongue-like section 54t passes on the coupling-ring disposing surface 28 and on an outer circumferential surface of the ring member 70 according to the movement of the distal-end bending die 51 and moves on the coupling-ring disposing surface 28 again. The flange contact surface 51f of the distal-end bending die 51 comes into contact with the coupling-ring contact surfaces 63f of the connecting pieces 60 provided in the connecting-piece-integrated illumination units 40Ua and 40Ub.

Figure 14:
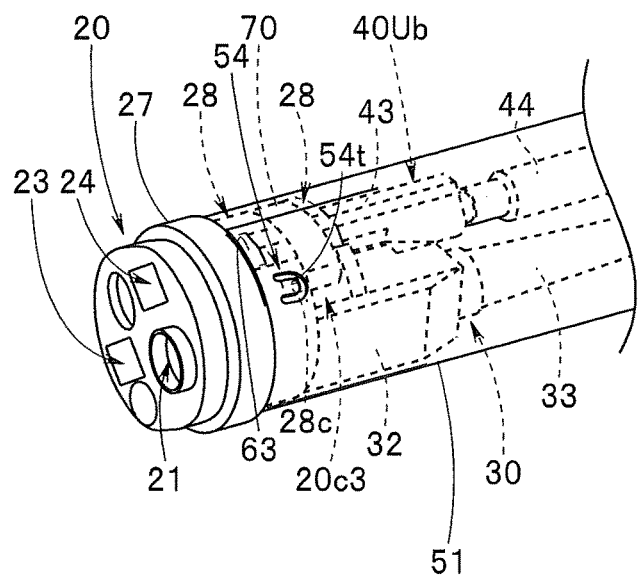
FIG. 14 is a diagram for explaining a state in which the distal-end rigid portion and a bending section set provided at a distal end portion of a flexible tube section are coupled and fixed.

The operator further moves the distal-end bending die 51 toward the rigid portion flange 27. Then, the tongue-like section 54t of the stepped tongue piece is engaged and disposed in the locking section 28c. As a result, as shown in FIG. 14, the distal-end rigid portion 20 and the bending section set 50 provided at the distal end portion of the flexible tube section 5 are coupled and fixed.

At this point, the distal end side flange 63 of the connecting piece 60 is held and fixed by the rigid portion flange 27 and the distal-end bending die 51. The recessed section 51c of the distal-end bending die 51 engages with the distal end side flange 63 of the connecting piece 60, whereby the distal-end bending die 51 is prevented from rotating around an axis of the distal-end rigid portion 20.

The distal-end bending die 51 covers the ring member 70, whereby the pressing projecting sections 73 set on the bottom surface of the recessed section for ring 64 of the connecting piece 60 press the first connecting-piece-integrated illumination unit 40Ua and the second connecting-piece-integrated illumination unit 40Ub in the center axis direction of the distal-end rigid portion 20.

As a result, the first connecting-piece-integrated illumination unit 40Ua and the second connecting-piece-integrated illumination unit 40Ub are fixed to positions determined in advance with respect to the axial direction and the circumferential direction of the distal-end rigid portion 20.

Thereafter, the operator performs, for example, work for assembling the distal end cover 6 to the distal-end rigid portion 20 and work for mounting the bending tube 4g on the bending section set 50. As a result, the insertion section 2 shown in FIG. 1 is configured.

In the assembly work, the operator can easily perform the work without rotating the distal-end rigid portion 20 and the bending section set 50. The internal components can be maintained in a stable state during the assembly work. Therefore, it is possible to stabilize quality.

In this way, the ring member 70 provided with the pressing projecting sections 73 is disposed in the circumferential direction groove for ring configured by the groove for ring setting 29 and the recessed section for ring 64. The connecting-piece-integrated illumination units 40Ua and 40Ub, which are the endoscope internal components, are provisionally fixed. Consequently, it is possible to greatly improve assembly workability.

In the provisionally fixed state, the distal-end bending die 51 is disposed in the coupling-ring disposing surface 28 of the distal-end rigid portion 20. The tongue-like section 54t of the distal-end bending die 51 is locked to the locking section 28c while covering the ring member 70. Consequently, it is possible to surely couple and fix the distal-end rigid portion 20 and the distal-end bending die 51 configuring the bending section set 50 provided at the distal end portion of the flexible tube section 5.

Figure 15:
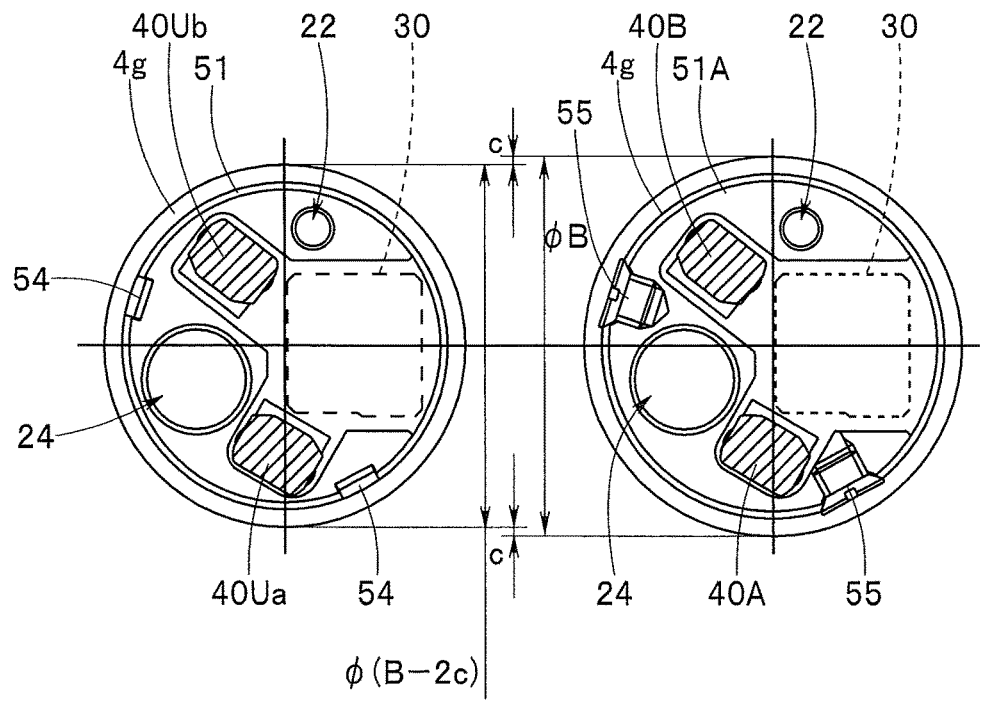
FIG. 15 is a diagram for explaining a difference in a diameter dimension of the distal-end rigid portion in a state in which, for example, an illumination unit, which is an endoscope internal component, is attached to the distal-end rigid portion using a fixing screw and a state in which the illumination unit is attached to the distal-end rigid portion without using the fixing screw.

In the coupled and fixed state, the distal end side flange 63 of the connecting piece 60 is held by the rigid portion flange 27 and the distal-end bending die 51. The pressing projecting sections 73 of the ring member 70 covered with the distal-end bending die 51 press the recessed sections for ring 64 of the connecting pieces 60 in the center axis direction. Consequently, it is possible to position the first connecting-piece-integrated illumination unit 40Ua and the second connecting-piece-integrated illumination unit 40Ub, which are the endoscope internal components, in the radial direction in a predetermined state in the distal-end rigid portion 20 without using a fixing screw as shown in FIG. 15. In addition, it is possible to fix the distal-end bending die 51 to the distal-end rigid portion 20 in a predetermined state without using a fixing screw.

As a result, compared with when the distal-end bending die 51 is fixed to a distal-end rigid portion 20A having an outer diameter 4B by a fixing screw 55 as shown in FIG. 15, in the distal-end rigid portion 20, it is possible to reduce thickness for forming a female thread for screwing the fixing screw 55 and reduce a diameter of the distal-end rigid portion 20 by a dimension 2c.

Note that, in the embodiment explained above, the connecting pieces 60 are provided in the illumination optical units 40A and 40B. However, the connecting pieces 60 may be provided in other endoscope internal components such as the observation optical unit 30. That is, a part of a cylindrical member including the connecting pieces 60 and the illumination optical units 40A and 40B may be pinched and fixed in an axial direction of the insertion section 2 between the distal-end rigid portion 20 and the distal-end bending die 51. In this case, the part of the cylindrical member engages in the recessed section 51c of the distal-end bending die 51 to prevent the distal-end bending die 51 from rotating around the axis of the distal-end rigid portion 20.

In the embodiment explained above, the ring member 70 provided with the pressing projecting sections 73 is disposed in the circumferential direction groove for ring configured by the groove for ring setting 29 and the recessed section for ring 64. The connecting-piece-integrated illumination units 40Ua and 40Ub are provisionally fixed. Then, the distal-end bending die 51 is fixed to the distal-end rigid portion 20. The connecting pieces 60 are pressed in the center axis direction by the pressing projecting sections 73 of the ring member 70.

Figure 16A:
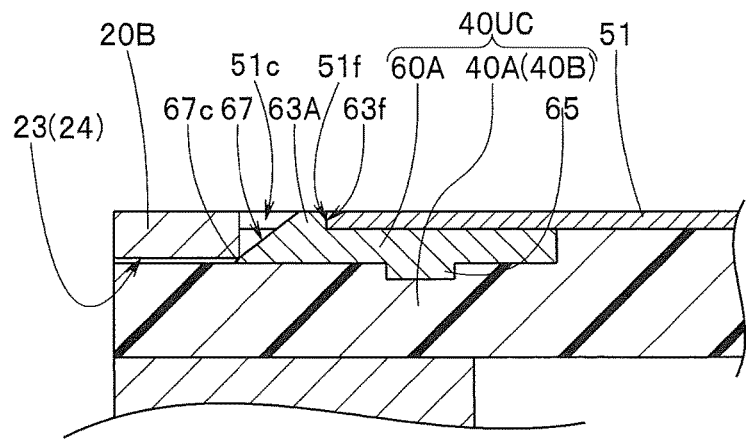
FIG. 16A is a diagram for explaining a configuration example in which, for example, a connecting-piece-integrated illumination unit, which is an endo scope internal component, is fixed to the distal-end rigid portion without using a ring member.

However, as shown in FIG. 16A, a connecting-piece-integrated illumination unit 40UC, in which connecting pieces 60A are respectively disposed in the illumination optical units 40A and 40B, may be configured. The illumination unit 40UC provided with the connecting pieces 60A may be fixed to the distal-end rigid portion 20B without using a fixing screw as explained above.

Figure 13B:
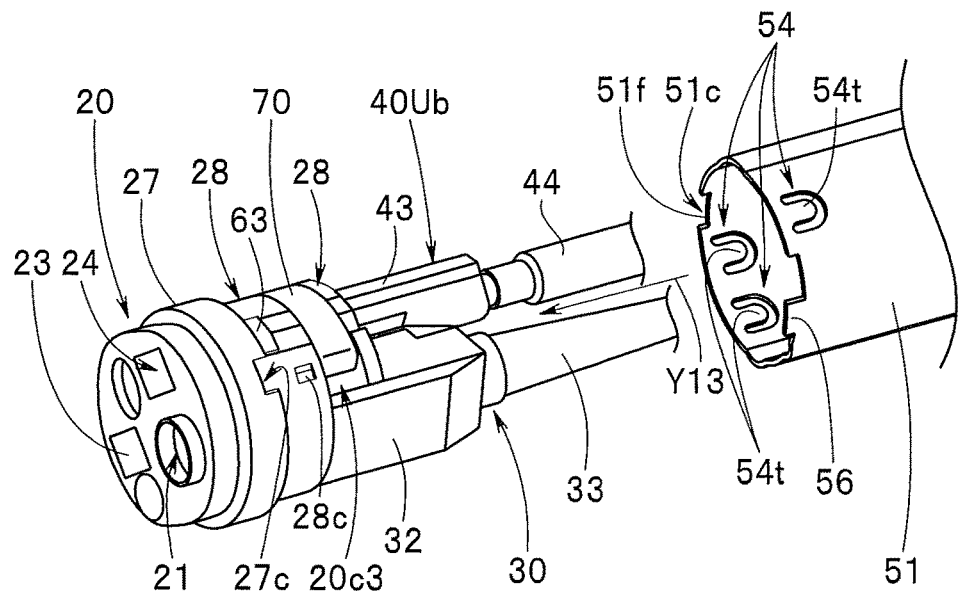
FIG. 13B is a diagram for explaining a configuration example in which a recessed section is further provided at the distal-end rigid portion in FIG. 13A and a projecting section is further provided at a distal end portion of the distal-end bending die.

In the embodiment explained above, the recessed section 51c of the distal-end bending die 51 engages with the distal end side flange 63 of the connecting piece 60 in FIG. 13A to prevent the distal-end bending die 51 from rotating around the axis of the distal-end rigid portion 20. However, as shown in FIG. 13B, a projecting section 56 may be further provided at the distal end portion of the distal-end bending die 51 and a recessed section 27c may be further provided in a proximal end portion of the rigid portion flange 27 of the distal-end rigid portion 20.

By engaging the projecting section 56 and the recessed section 27c, it is possible to surely prevent the distal-end bending die 51 from rotating around the axis with respect to the distal-end rigid portion 20.

In the present embodiment, in the connecting piece 60A, an inclined surface 67 is provided on a distal end face of a distal end side flange 63A configuring a distal end side and, then, an engaging projecting section 67c is provided at a distal end portion of the inclined surface 67. On the other hand, a proximal end side end of the retaining hole 23 or 24 of a distal-end rigid portion 20B is set as a contact section 20e that is in contact with the inclined surface 67.

The other components are the same as the components in the embodiment explained above. The same members are denoted by the same reference numerals and explanation of the members is omitted.

According to this configuration, first, the connecting-piece-integrated illumination unit 40UC is disposed in, for example, the first retaining hole 23. Thereafter, the inclined surface 67 is moved to the contact section 20e side while setting the flange contact surface 51f of the distal-end bending die 51 in contact with the coupling-ring contact surface 63f of the connecting piece 60A configuring the connecting-piece-integrated illumination unit 40UC. Then, the engaging projecting section 67c intrudes into the retaining hole 23 or 24, the contact section 20e comes into contact with the inclined surface 67, and the tongue-like section 54t is engaged and disposed in the locking section 28c. As a result, the distal end side flange 63A is held by the contact section 20e and the flange contact surface 51f. The contact section 20e presses the inclined surface 67 in the center axis direction. It is possible to fix the connecting-piece-integrated illumination unit 40UC to the distal-end rigid portion 20B in a predetermined state without using a fixing screw as explained above.

Figure 16B:
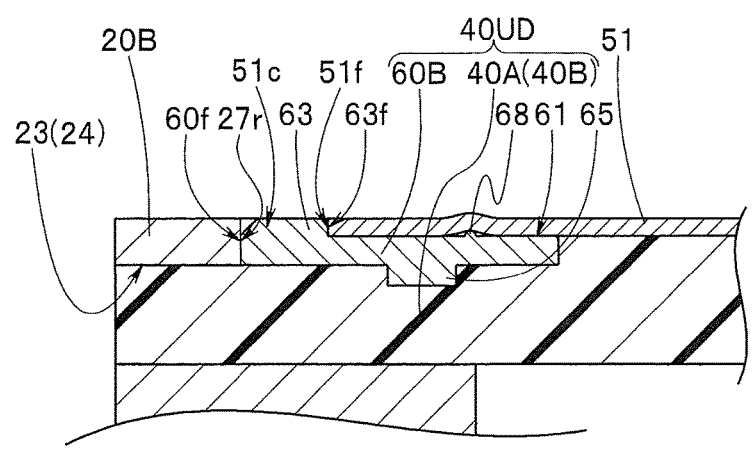
FIG. 16B is a diagram for explaining a configuration example in which, for example, a connecting-piece-integrated illumination unit, which is an endo scope internal component, is fixed to the distal-end rigid portion without using a ring member.

As shown in FIG. 16B, a connecting-piece integrated illumination unit 40UD, in which connecting pieces 60B are respectively provided in the illumination optical units 40A and 40B, may be configured. The illumination unit 40UD may be fixed to the distal-end rigid portion 20B without using a fixing screw as explained above.

The connecting piece 60B is configured by providing a pressing projecting section 68 on the first surface 61 on which the distal-end bending die 51 is disposed instead of providing the inclined surface 67 in the distal end side flange 63. The other components are the same as the components in the embodiment explained above.

According to this configuration, first, the connecting-piece-integrated illumination unit 40UD is disposed in, for example, the first retaining hole 23. Thereafter, the distal-end bending die 51 is disposed to cover the first surface 61 of the connecting piece 60B. The distal-end bending die 51 is moved in a direction of the flange abutting surface 27r. Then, an inner surface of the distal-end bending die 51 passes on the pressing projecting section 68. Thereafter, the flange contact surface 51*f* comes into contact with the coupling-ring contact surface 63*f*. The distal end side flange 63 is brought into contact with the flange abutting surface 27*r*. The tongue-like section 54*t* is engaged and disposed in the locking section 28*c*.

As a result, the distal end side flange 63 is held by the flange abutting surface 27*r* and the flange contact surface 51*f*. The pressing projecting section 68 is pressed in the center axis direction by the distal-end bending die 51 externally fit and disposed in the connecting piece 60B. It is possible to fix the connecting-piece-integrated illumination unit 40UD to the distal-end rigid portion 20B in a predetermined state without using a fixing screw as explained above.

Note that, in the present embodiment, at a point in time when the inner surface of the distal-end bending die 51 passes on the pressing projecting section 68, the connecting-piece-integrated illumination unit 40UD is provisionally fixed to the distal-end rigid portion 20B. That is, the distal-end bending die 51 is also used as the ring member 70.

Figure 16C:
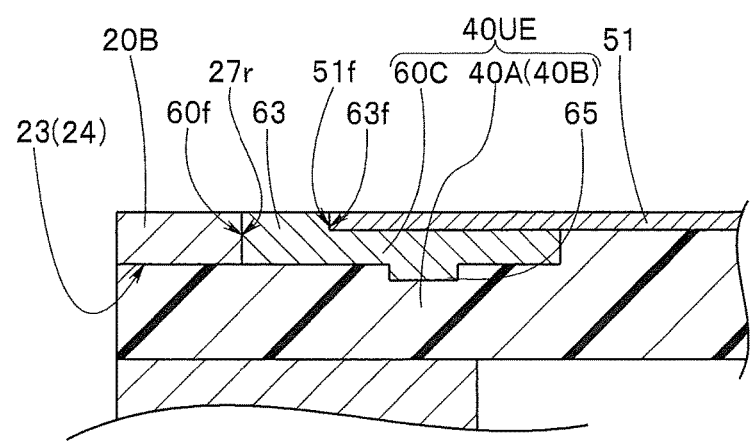
FIG. 16C is a diagram for explaining a configuration example in which, for example, a connecting-piece-integrated illumination unit, which is an endo scope internal component, is fixed to the distal-end rigid portion without using a ring member.

As shown in FIG. 16C, connecting pieces 60C may be configured without providing the recessed section for ring 64, the inclined surface 67, and the pressing projecting section 68. The connecting pieces 60C may be respectively disposed in the illumination optical units 40A and 40B to configure a connecting-piece-integrated illumination unit 40UE.

In this configuration, first, the connecting-piece-integrated illumination unit 40UE is disposed in, for example, the first retaining hole 23. Thereafter, the distal-end bending die 51 is disposed to cover the first surface 61 of the connecting piece 60C. The distal-end bending die 51 is moved in the direction of the flange abutting surface 27*r* to bring the flange contact surface 51*f* into contact with the coupling-ring contact surface 63*f*. The distal end side flange 63 is brought into contact with the flange abutting surface 27*r*. The tongue-like section 54*t* is engaged and disposed in the locking section 28*c*.

As a result, the distal end side flange 63 is held by the flange abutting surface 27*r* and the flange contact surface 51*f*. The second surface 62 of the connecting piece 60C is pressed in the center axis direction by the externally fit and disposed distal-end bending die 51. It is possible to fix the connecting-piece-integrated illumination unit 40UD to the distal-end rigid portion 20B in a predetermined state without using a fixing screw as explained above.

That is, according to the configurations of FIG. 16A, FIG. 16B and FIG. 16C, the connecting-piece-integrated illumination unit is fixed to the distal-end rigid portion without using the ring member 70.

Note that the insertion apparatus is not limited to the endoscope and is a member including an elongated insertion section such as a guide tube or a treatment instrument.

The observation optical unit 30 and the illumination optical units 40A and 40B are disposed in the distal end portion 3 of the insertion section 2 described above. The units 30, 40A, and 40B include substrates mounted with electronic components. Distal ends of pluralities of signal lines are connected to contact sections of the substrates. The distal ends of the signal lines are likely to separate from the substrates when the distal ends receive external force due to bending, twisting, or the like of the insertion section 2.

As shown in FIGS. 17A, 17B, 18A, and 18B, an apparatus 110 includes an electronic component unit 125. The electronic component unit 125 is configured by a plurality of components and includes an electronic module 130 and a connection cable 140 connected to the electronic module 130. The electronic component unit 125 includes a cable fixing mechanism 150 that fixes the connection cable 140 to a substrate 131 of the module 130.

Note that an example of the apparatus 110 is the endoscope 1 explained above. The insertion section 2 is provided in the endoscope 1. The bending section 4 or the flexible tube section 5 is included in the insertion section 2. The electronic module 130 and the connection cable 140 function as components of the electronic component unit 125 incorporated in the insertion section 2. The electronic component unit 125 is the observation optical unit 30 and the illumination optical units 40A and 40B explained above.

The electronic module 130 includes, for example, the substrate 131 and an element 133. The element 133 is fixed to a distal end face of the substrate 131 by, for example, not-shown solder.

When the electronic component unit 125 is the illumination unit, the element 133 is a light emitting element such as an LED. When the electronic component unit 125 is an image pickup unit, the element 133 is an image pickup device such as a CMOS.

When the signal element 133 is the light emitting element, electric power is supplied by electric wires 141 of the electric cable 140. The electric cable 140 includes the electric wires 141 electrically connected to the substrate 131 and an outer layer section 143 disposed on the outer side of the electric wires 141. The outer layer section 143 collectively covers an outer circumference of a plurality of electric wires 141.

The outer layer section 143 includes a shield member 145 and an outer skin 147. The shield member 145 is a comprehensive shield. The shield member 145 is disposed on an outer side of the electric wires 141 and collectively covers the plurality of electric wires 141. The outer skin 147 is disposed on an outer side of the shield member 145 and further covers the shield member 145. The electric wires 141 and the shield member 145 are made of, for example, metal having conductivity. The outer skin 147 is made of, for example, resin having electric insulation properties.

The electric cable 140 in the present embodiment includes two electric wires 141. However, a plurality of signal lines and a plurality of electric wires may be disposed in the electric cable 140. The electric wires 141 and the signal lines have flexibility and have, for example, a circular sectional shape. Note that, as shown in FIG. 20B and FIG. 20C referred to below, a core wire bundle obtained by forming element wires as a bundle is included in the electric wires 141.

Figure 17A:
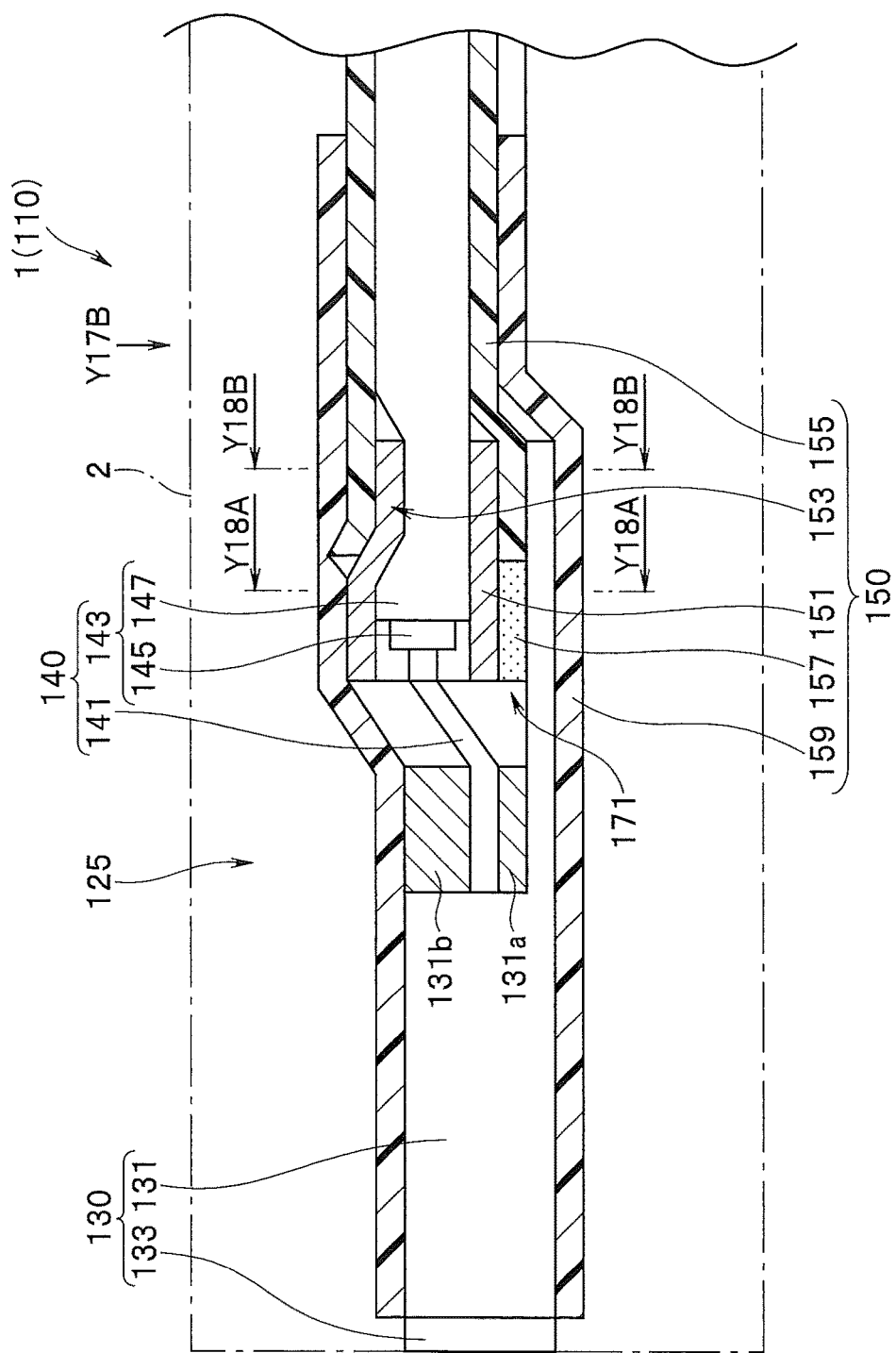
FIG. 17A is a diagram of a structure of an electronic component unit viewed from a side surface side.
Figure 17B:
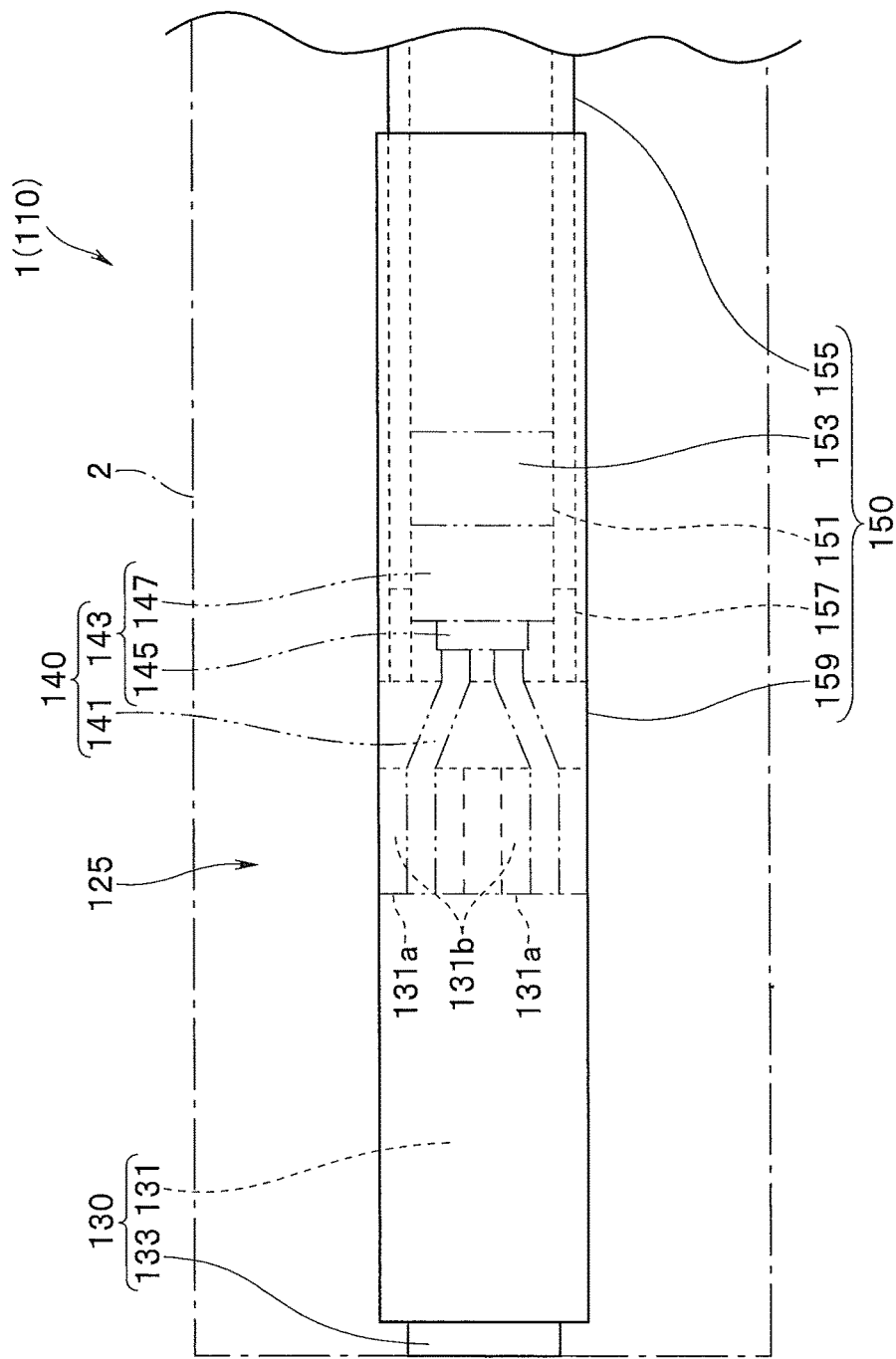
FIG. 17B is a diagram of the electronic component unit viewed from an arrow Y17B direction shown in FIG. 17A.

As shown in FIG. 17A and FIG. 17B, distal end portions of the electric wires 141 are exposed from a distal end of the shield member 145, a distal end of the outer skin 147, and a distal end of a cover member 151 explained below. That is, in the electric wires 141, a distal end portion of the shield member 145 and a distal end portion of the outer skin 147 are removed.

In the connection cable 140 and the cover member 151, the connection cable 140 is inserted into the cover member 151 such that the distal end portions of the electric wires 141 are exposed from a distal end of the cover member 151.

The distal end portions of the electric wires 141 are placed in a groove section 1131*a* provided on the substrate 131 and are fixed to the substrate 131 by, for example, solder 131*b*. As a result, the electric wires 141 are electrically connected to the element 133 via the substrate 131. The solder 131*b* is filled in the groove section 1131*a*.

Figure 18A:
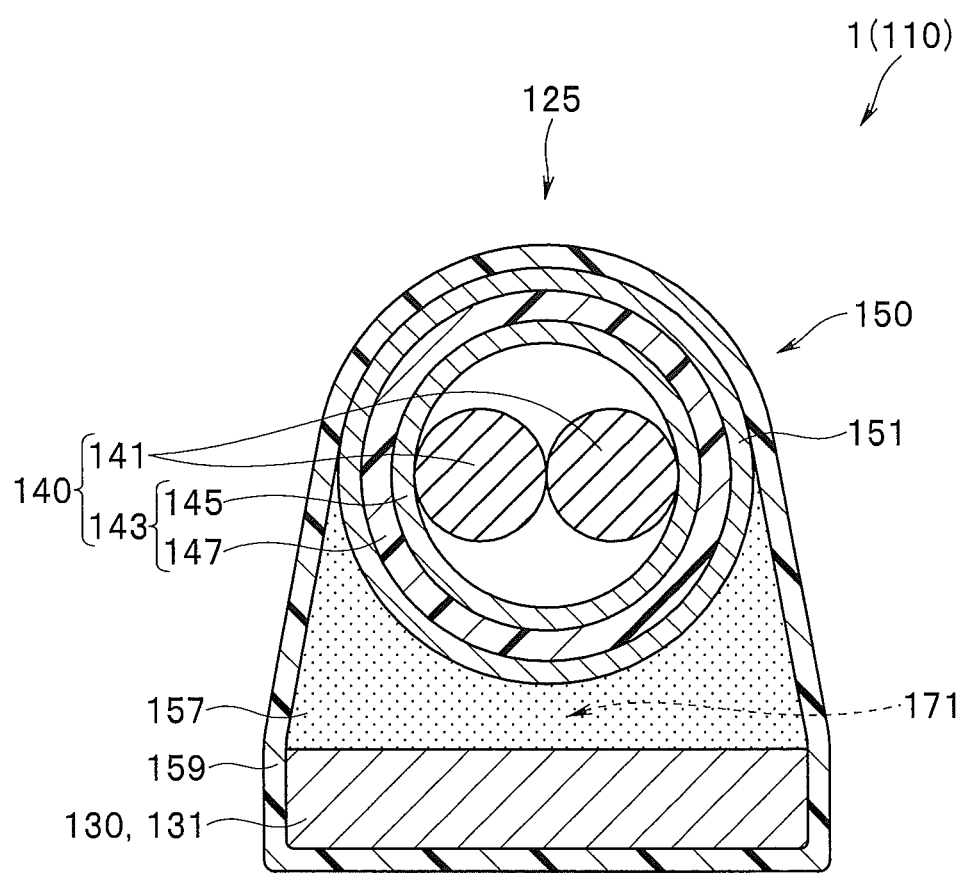
FIG. 18A is a sectional view of the electronic component unit along an arrow Y18A-Y18A line shown in FIG. 17A.

The shield member 145 shown in FIG. 18A is formed as a mesh-like tube by intertwining a plurality of element wires made of metal. The electric wires 141 are insertable through the shield member 145.

The shield member 145 electrically protects the electric wires 141 such that noise caused from a not-shown external apparatus such as an electric knife that is a high-frequency treatment instrument for endoscope does not electrically affect the electric wires 141.

As shown in FIG. 17A and FIG. 17B, in the present embodiment, the distal end portion of the shield member 145 is exposed forward from the distal end of the outer skin 147 along a longitudinal axis direction.

In the connection cable 140, the distal end portion of the outer skin 147 of the connection cable 140 is removed such that the distal end portion of the shield member 145 is exposed from the distal end of the outer skin 147.

Although not shown in the figure, the distal end portion of the shield member 145 may be positioned in a position same as the distal end portion of the outer skin 147 or may be folded back to overlap an outer circumferential surface of the distal end portion of the outer skin 147.

As shown in FIG. 18A, the outer skin 147 is formed as, for example, a tube made of resin having electric insulation properties. An inner circumferential surface of the outer skin 147 is closely attached to an outer circumferential surface of the shield member 145.

As shown in FIGS. 17A, 17B, 18A, and 18B, the cable fixing mechanism 150 positions and fixes the electric wires 141 to prevent movement of the connection cable 140 including the electric wires 141 and fixes the connection cable 140 to the substrate 131 of the electronic module 130.

The cable fixing mechanism 150 further includes a crimping and fixing section 153. The crimping and fixing section 153 includes the cover member 151 through which a distal end portion of the connection cable 140 is inserted. The crimping and fixing section 153 is disposed in the cover member 151 and formed by crimping a part of the cover member 151 such that the part of the cover member 151 is sandwiched by one electric wire 141 and the other electric wire 141.

That is, the crimping and fixing section 153 positions and fixes the one electric wire 141 and the other electric wire 141 with respect to the cover member 151 through the crimping and fixes the cover member 151 to the electric wires 141 through the crimping.

The cable fixing mechanism 150 further includes a proximal-end-side protection member 155. The proximal-end-side protection member 155 is disposed on an outer side of the outer skin 147 of the connection cable 140 and an outer side of a proximal end portion of the cover member 151. The proximal-end-side protection member 155 functions as a cover member that covers and protects the outer skin 147 and the proximal end portion of the cover member 151.

The cable fixing mechanism 150 includes a fixing member 157 having insulation properties that fixes the cover member 151 to the substrate 131.

The cable fixing mechanism 150 further includes a distal-end-side protection member 159. The distal-end-side protection member 159 functions as a cover member that covers and protects the entire substrate 131, the distal end portions of the electric wires 141, the cover member 151, and the distal end portion side of the connection cable 140 including a distal end portion side of the proximal-end-side protection member 155.

The connection cable 140 is inserted into the cover member 151. An inner diameter of the cover member 151 is equal to or larger than an outer diameter of the connection cable 140 such that the connection cable 140 is inserted through the cover member 151. The cover member 151 is connected to the connection cable 140 by the crimping and fixing section 153 and the proximal-end-side protection member 155. Such a cover member 151 includes a pipe formed of, for example, a metal material.

Like the shield member 145, the cover member 151 electrically protects the electric wires 141 such that the noise caused from the electric knife does not electrically affect the electric wires 141. The cover member 151 functions as a shield member as well.

The cover member 151 covers the distal end portion of the connection cable 140 such that the distal end portions of the electric wires 141 are exposed from the distal end of the cover member 151, the distal end portion of the shield member 145 and the distal end portion of the outer skin 147 are not exposed from the distal end of the cover member 151, and the distal end portion of the cover member 151 covers the distal end portion of the shield member 145 and the distal end portion of the outer skin 147. A reason for exposing the distal end portions of the electric wires 141 from the cover member 151 is to connect the electric wires 141 to the electronic module 130.

Figure 18B:
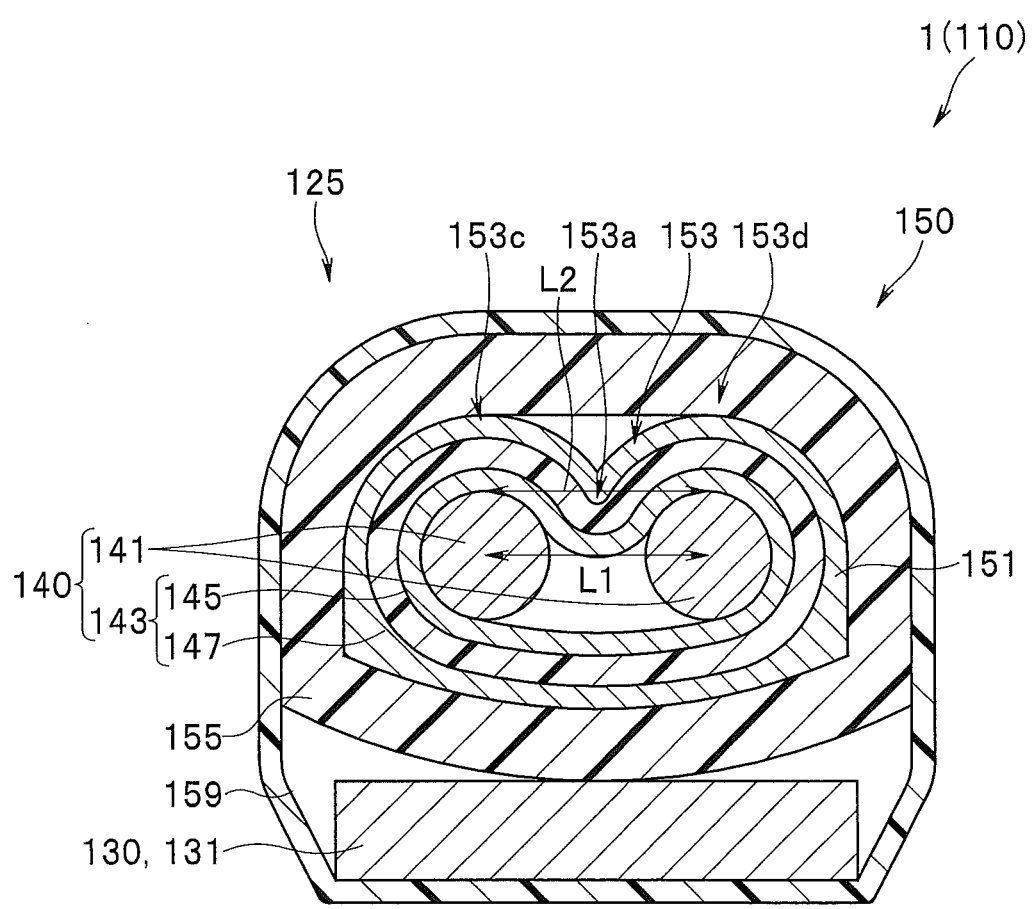
FIG. 18B is a sectional view of the electronic component unit along an arrow Y18B-Y18B line shown in FIG. 17A.

In the cover member 151, the proximal end portion of the cover member 151 including the crimping and fixing section 153 is protected by a distal end portion of the proximal-end-side protection member 155 such that the distal end portion of the cover member 151 is exposed from the distal end of the proximal-end-side protection member 155. As shown in FIG. 17A, FIG. 17B, and FIG. 18B, the crimping and fixing section 153 is disposed at the proximal end portion of the cover member 151 protected by the distal end portion of the proximal-end-side protection member 155 such that the crimping and fixing section 153 is covered by the distal end portion of the proximal-end-side protection member 155. In other words, the cover member 151 includes the crimping and fixing section 153 disposed in the proximal end portion of the cover member 151.

As shown in FIG. 18B, in the crimping and fixing section 153, the crimping is implemented by, for example, a jig. The crimping is implemented toward an up-down direction in the figure, in other words, a radial direction of the cover member 151, in other words, a direction orthogonal to a longitudinal axis of the cover member 151. In this case, for example, the proximal end portion of the cover member 151 is placed on a not-shown tabular member.

In a state in which the proximal end portion of the cover member 151 is placed on the tabular member, a part of the cover member 151 is crimped and deformed to be sandwiched by the one electric wire 141 and the other electric wire 141. The crimping and fixing section 153 sandwiched by the one electric wire 141 and the other electric wire 141 is formed by the deformation. In this case, for example, 10% or more of an original diameter of the cover member 151 is crushed at the proximal end portion of the cover member 151 by the crimping.

A sectional shape of the crimping and fixing section 153 is formed as a noncircular shape. Therefore, in the cover member 151, the proximal end portion of the cover member 151, in which the crimping and fixing section 153 is formed, includes the crimping and fixing section 153 having the noncircular shape.

In the crimping and fixing section 153, a part of the cover member 151 penetrates between the one electric wire 141 and the other electric wire 141, whereby a constricted section 153*a* is formed.

The constricted section 153a is formed by constricting a part of an inner circumferential surface of the crimping and fixing section 153 toward a center of a cross section of the proximal end portion of the cover member 151 to narrow and recess the entire crimping and fixing section 153.

Therefore, the electric wires 141 are positioned and fixed to the cover member 151 on the inside of the cover member 151.

In the cover member 151, the constricted section 153a is formed in the crimping and fixing section 153 by the jig and, at the same time, a bottom surface side of the cover member 151 opposed to the tabular member is pressed toward the tabular member, whereby a cross section on the bottom surface side of the cover member 151 is crimped to be deformed from an arcuate shape into a substantially plane shape and integrally fixed to the connection cable 140.

Such a sectional shape of the crimping and fixing section 153 is formed in a numeral "3" shape. A sectional shape of the proximal end portion of the cover member 151 including the crimping and fixing section 153 is formed in, for example, a "B" shape by the crimping and fixing section 153. In this case, the crimping and fixing section 153 having the numeral "3" shape is disposed on an opposite side of the bottom surface side of the cover member 151 having the substantially plane shape across the electric wires 141 in a thickness direction of the substrate 131.

As shown in FIG. 18B, in a state in which the crimping is implemented, a straight line connecting a center of the one electric wire 141 and a center of the other electric wire 141 is represented as L1.

A straight line disposed in parallel to the straight line L1 and connecting an outer circumferential surface of the one electric wire 141 and an outer circumferential surface of the other electric wire 141 is represented as L2. The straight line L2 is, for example, a tangent line connecting the one electric wire 141 and the other electric wire 141.

The constricted section 153a is suitably formed such that an inner circumferential part of the cover member 151 located in the constricted section 153a is located between the straight line L1 and the straight line L2.

In the present embodiment, the crimping and fixing section 153 including the constricted section 153a includes a first adhering section 153c and a second adhering section 153d. The first adhering section 153c indirectly adheres to substantially a half of the outer circumference of the one electric wire 141. The second adhering section 153d indirectly adheres to substantially a half of the outer circumference of the other electric wire 141.

The first adhering section 153c is adjacent to the second adhering section 153d such that the constricted section 153a is interposed between the first adhering section 153c and the second adhering section 153d in a direction orthogonal to a crimping implementing direction, for example, in a width direction of the substrate 131.

The first adhering section 153c is concatenated to the second adhering section 153d. The first adhering section 153c and the second adhering section 153d have a shape conforming to the outer circumference of the electric wires 141. As explained above, the sectional shape of the electric wires 141 is formed in the circular shape. Therefore, the first adhering section 153c and the second adhering section 153d have, for example, a U-shape to correspond to the sectional shape.

In this way, the crimping and fixing section 153 including the constricted section 153a is continuously disposed in a linear shape along a longitudinal axis direction of the cover member 151 as shown in FIG. 17A and FIG. 17B rather than being disposed in a spot shape. The crimping and fixing section 153 including the constricted section 153a has length twice or more as large as a diameter of the electric wires 141 in a longitudinal axis direction of the connection cable 140. More specifically, the crimping and fixing section 153 has, for example, ⅓ length of total length of the cover member 151. The crimping and fixing section 153 is disposed, for example, between a portion located in a position of ⅔ of the total length of the cover member 151 from the distal end of the cover member 151 and a proximal end of the cover member 151. For example, the crimping and fixing section 153 is disposed in the entire cover member 151 protected by the proximal-end-side protection member 155 in the longitudinal axis direction of the cover member 151.

Note that, in the present embodiment, the proximal end portion of the cover member 151 including the crimping and fixing section 153 covers the shield member 145 and the outer skin 147, which are the outer layer section 143, in the connection cable 140. Therefore, as shown in FIG. 18B, when a part of the cover member 151 is crimped, a part of the shield member 145 and a part of the outer skin 147, which are the outer layer section 143, are also crimped to be sandwiched by the one electric wire 141 and the other electric wire 141 together with the part of the cover member 151.

The crimping and fixing section 153 crimps, together with the proximal end portion of the cover member 151, like the proximal end portion of the cover member 151, the shield member 145 and the outer skin 147 covered by the proximal end portion of the cover member 151. In other words, the crimping and fixing section 153 indirectly crimps the electric wires 141 via a part of the outer layer section 143. Further, in other words, the crimping and fixing section 153 is disposed on the cover member 151, the shield member 145, and the outer skin 147. The crimping and fixing section 153 closely attaches the crimped part of the outer layer section 143 to a part of an outer circumferential surface of the electric wires 141. The shield member 145 and the outer skin 147 have a configuration, a shape, and the like same as the configuration, the shape, and the like of the crimping and fixing section 153 explained above.

Note that, in the outer layer section 143 and the cover member 151, a crimping direction is not limited to the direction explained above. The crimping may be implemented in an oblique direction skewing with respect to the longitudinal axis of the cover member 151 to match an intertwining direction of the element wires of the shield member 145.

As shown in FIG. 18B, such a crimping and fixing section 153 closely attaches the respective electric wires 141 to an inner circumferential surface of the shield member 145 through the crimping and increases an adhesion area or density from a state before the crimping is implemented. Consequently, the crimping and fixing section 153 prevents the electric wires 141 from moving in a longitudinal axis direction of the wires 141 and a radial direction of the wires 141, prevents the electric wires 141 from being twisted, and prevents the position of the electric wires 141 on an inside of the shield member 145 from shifting in position.

As a result, in a state in which the electric wires 141 are separated from each other, the crimping and fixing section 153 fixes the electric wires 141 to the shield member 145 and positions and fixes the electric wires 141 with respect to the cover member 151. The crimping and fixing section 153 fixes the cover member 151 to the connection cable 140.

When the insertion section 2 receives external force, stress is generated in the connection cable 140. Then, the connection cable 140 is about to move in the longitudinal axis direction of the connection cable 140 and a radial direction of the connection cable 140, about to be twisted, and about to further extend or shrink with the stress.

When the movement, the twisting, and the extension and shrinkage are transmitted to the distal end portions of the electric wires 141 exposed from the distal end portion of the cover member 151, it is likely that the distal end portions of the electric wires 141 shift in position and separate from the substrate or the electric wires 141 is ruptured and the element 133 causes malfunction. However, in the present embodiment, the crimping and fixing section 153 is disposed. The crimping and fixing section 153 prevents, through the crimping, the movement, the twisting, and the extension and shrinkage from being transmitted to the distal end portions of the electric wires 141, prevents the positional shift of the distal end portions of the electric wires 141, and fixes the distal end portions of the electric wires 141. As a result, the crimping and fixing section 153 prevents the distal end portions of the electric wires 141 from separating from the substrate, prevents the electric wires 141 from being ruptured and broken, and prevents occurrence of malfunction of the element 133.

As shown in FIG. 17A, the distal end portion side of the connection cable 140 is covered by the cover member 151. In this state, the proximal-end-side protection member 155 protects the connection cable 140 including the proximal end portion of the cover member 151 such that the distal end portion of the cover member 151 is exposed from the distal end of the proximal-end-side protection member 155.

Note that the distal end portion of the proximal-end-side protection member 155 only has to protect at least the crimping and fixing section 153 in the cover member 151. The proximal-end-side protection member 155 may be included in the connection cable 140.

The proximal-end-side protection member 155 has electric insulation properties. The proximal-end-side protection member 155 is suitably formed by, for example, a heat shrinkable tube or a fluorine-based resin tube that is tubular and has shrinkability such that the connection cable 140 and the cover member 151 are inserted into the proximal-end-side protection member 155.

When the proximal-end-side protection member 155 is formed by the heat shrinkable tube, heat is applied to shrink the proximal-end-side protection member 155. An inner circumferential surface of the proximal-end-side protection member 155 adheres to an outer circumferential surface of the cover member 151 and an outer circumferential surface of the outer skin 147 of the connection cable 140.

Consequently, the proximal-end-side protection member 155 protects the proximal end portion of the cover member 151 and the distal end portion of the connection cable 140. At the same time, the proximal-end-side protection member 155 fixes the cover member 151 to the distal end portion of the connection cable 140 without using an adhesive or the like. In other words, the proximal-end-side protection member 155 assists fixing of the cover member 151 fixed to distal end portion of the connection cable 140 by the crimping and fixing section 153.

As shown in FIG. 17A and FIG. 17B, the distal end portion of the proximal-end-side protection member 155 is placed on the substrate 131. The distal end portion of the cover member 151 exposed from the distal end portion of the proximal-end-side protection member 155 is apart from the substrate 131 by thickness of the proximal-end-side protection member 155 in the thickness direction of the substrate 131 according to the thickness of the proximal-end-side protection member 155. The distal end portion of the cover member 151 is insulated from the substrate 131.

Therefore, the proximal-end-side protection member 155 forms a space section 171 between the cover member 151 and the substrate 131 in the thickness direction of the substrate 131 and secures insulation of the cover member 151 from the substrate 131.

Note that, on the proximal end portion side of the proximal-end-side protection member 155, the proximal-end-side protection member 155 protects the connection cable 140 up to a position beyond a proximal end of the bending section 4 disposed in the insertion section 2. The position beyond the proximal end of the bending section 4 is, for example, a coupling pipe sleeve section that couples the proximal end of the bending section 4 and a distal end of the flexible tube section 5.

The fixing member 157 fixes the distal end portion of the cover member 151 to the substrate 131. Therefore, the fixing member 157 is disposed between at least a part of the outer circumferential surface of the cover member 151 and the substrate 131 in the thickness direction of the substrate 131.

The distal end portion of the cover member 151 exposed from the distal end portion of the proximal-end-side protection member 155 is apart from the substrate 131 by the thickness of the proximal-end-side protection member 155 in the thickness direction of the substrate 131 according to the thickness of the proximal-end-side protection member 155. In the thickness direction of the substrate 131, the space section 171 is formed between the cover member 151 and the substrate 131. Therefore, the fixing member 157 is disposed in the space section 171 and between the bottom surface side of the cover member 151 opposed to the substrate 131 and the substrate 131 in the thickness direction of the substrate 131.

As shown in FIG. 17A, the fixing member 157 is not disposed in front of the distal end portion of the cover member 151, more specifically, on the distal end portion side of the electric wires 141 exposed from the distal end portion of the cover member 151. The fixing member 157 is not disposed between the proximal-end-side protection member 155 and the substrate 131.

In this way, the fixing member 157 is disposed only in a portion corresponding to the cover member 151 exposed from the proximal-end-side protection member 155.

The fixing member 157 is formed as, for example, an ultraviolet curing-type adhesive member that is irradiated with UV light from a side direction of the fixing member 157 to harden and fixes the cover member 151 to the substrate 131 through the hardening. The side direction indicates, for example, a direction orthogonal to the thickness direction of the substrate 131 and the longitudinal axis direction of the cover member 151. More specifically, the side direction indicates a left-right direction in FIG. 18A.

Note that the fixing member 157 may be formed by an epoxy-based adhesive. The fixing member 157 may include thermoplastic resin that melts with heat and hardens in a natural state.

The fixing member 157 has insulation properties. The cover member 151 is fixed to the substrate 131 while being insulated from the substrate 131.

The distal-end-side protection member 159 shown in FIG. 17A, FIG. 17B, FIG. 18A, and FIG. 18B is tubular and has shrinkability. The substrate 131, the cover member 151, or the proximal-end-side protection member 155 is inserted into the distal-end-side protection member 159. The distalend-side protection member 159 is suitably formed by, for example, a heat shrinkable tube or a fluorine-based resin tube.

When the distal-end-side protection member 159 is formed by the heat shrinkable tube, heat is applied to shrink the distal-end-side protection member 159. An inner circumferential surface of the distal-end-side protection member 159 adheres to a circumferential surface of the substrate 131, a circumferential surface of the distal end portions of the electric wires 141, a circumferential surface of the cover member 151, and a circumferential surface of the proximal-end-side protection member 155. Consequently, the distal-end-side protection member 159 protects the entire substrate 131, the distal end portions of the electric wires 141, the cover member 151, and the proximal-end-side protection member 155. At the same time, the distal-end-side protection member 159 fixes the cover member 151 to the substrate 131 and fixes the proximal-end-side protection member 155 to the substrate 131 without using an adhesive or the like. In other words, the distal-end-side protection member 159 assists fixing of the cover member 151 fixed to distal end portion of the connection cable 140 by the crimping and fixing section 153 and the proximal-end-side protection member 155.

The distal-end-side protection member 159 assists close attachment of the proximal-end-side protection member 155 closely attached to the distal end portion of the connection cable 140 by heat shrinkage. The distal-end-side protection member 159 assists fixing of the cover member 151 fixed to the substrate 131 by the fixing member 157. The distal-end-side protection member 159 assists fixing of the distal end portions of the electric wires 141 fixed to the substrate 131 by solder 31*b*.

In the above explanation, the distal-end-side protection member 159 protects the entire substrate 131 and secures strength of the substrate 131.

In this state, as shown in FIG. 17A, the distal-end-side protection member 159 has desired length in an axial direction of the distal-end-side protection member 159. More specifically, the distal-end-side protection member 159 is disposed such that a distal end portion of the distal-end-side protection member 159 is located in front of the distal end portions of the electric wires 141 and a proximal end portion of the distal-end-side protection member 159 is located behind the proximal end portion of the substrate 131 along the longitudinal axis direction. In other words, the proximal end portion of the distal-end-side protection member 159 is located behind the proximal end portion of the substrate 131. The proximal end portion of the substrate 131 is located behind the fixing member 157.

Therefore, the distal-end-side protection member 159 sufficiently prevents the fixing member 157 from leaking out to an outside of the distal-end-side protection member 159.

Like the shield member 145, the distal-end-side protection member 159 electrically insulates the substrate 131 and the electric wires 141 such that the noise caused from the electric knife or the like does not electrically affect the substrate 131 and the electric wires 141.

The distal-end-side protection member 159 has insulation properties as explained above and secures insulation from not-shown other components disposed around the substrate 131.

Note that, taking into account the fact that the substrate 131 discharges heat generated when the element 133 is driven, the distal-end-side protection member 159 may protect the substrate 131 such that the distal end portion of the substrate 131 is exposed from the distal end portion of the distal-end-side protection member 159.

A distal end portion of a connection cable 40 is inserted into a cover member 51. At this point, the cover member 51 covers the distal end portion of the connection cable 40 such that a distal end portion of a core wire section 41 is exposed from a distal end portion of the cover member 51, a distal end portion of a shield member 45 and a distal end portion of an outer skin 47 are not exposed from the distal end portion of the cover member 51, and the distal end portion of the cover member 51 covers the distal end portion of the shield member 45 and the distal end portion of the outer skin 47. As shown in FIG. 18B, a part of the shield member 145, a part of the outer skin 147, and a part of the cover member 151 are crimped. The crimping and fixing section 153 including the constricted section 153*a* is formed. At this point, the first adhering section 153*c* adheres to substantially a half of the outer circumference of the one electric wire 141 and the second adhering section 153*d* adheres to substantially a half of the outer circumference of the other electric wire 141.

The crimping and fixing section 153 closely attaches the respective electric wires 141 to the inner circumferential surface of the shield member 145 through the crimping and increases an adhesion area or density from a state before the crimping is implemented. Consequently, the crimping and fixing section 153 prevents the electric wires 141 from moving in the longitudinal axis direction of the wires 141 and the radial direction of the wires 141, prevents the electric wires 141 from being twisted, and prevents the electric wires 141 on the inside of the shield member 145 from shifting in position.

As a result, in a state in which the electric wires 141 are separated from each other, the crimping and fixing section 153 fixes the electric wires 141 to the shield member 145 and positions and fixes the electric wires 141 with respect to the cover member 151. The crimping and fixing section 153 fixes the cover member 151 to the connection cable 140.

When the insertion section 2 receives external force, stress is generated in the connection cable 140. Then, the connection cable 140 is moved in the longitudinal axis direction of the connection cable 140 or the radial direction of the connection cable 140, or is twisted, or is extended or shrunk by the stress. When the movement, the twisting, and the extension and shrinkage are transmitted to the distal end portions of the electric wires 141 exposed from the distal end portion of the cover member 151, it is likely that the distal end portions of the electric wires 141 shift in position and separate from the connection substrate or the electric wires 141 is ruptured or broken and the element 133 causes malfunction. However, in the present embodiment, the crimping and fixing section 153 is disposed. The crimping and fixing section 153 prevents, through the crimping, the movement, the twisting, and the extension and shrinkage from being transmitted to the distal end portions of the electric wires 141, prevents the positional shift of the distal end portions of the electric wires 141, and fixes the distal end portions of the electric wires 141. Therefore, the crimping and fixing section 153 prevents the distal end portions of the electric wires 141 from separating from the connection substrate, prevents the electric wires 141 from being ruptured or broken, and prevents occurrence of malfunction of the element 133.

The crimping and fixing section 153 functions as a rigid portion. However, the crimping and fixing section 153 more firmly and surely fixes the electric wires 141 in a shorter range along the longitudinal axis direction than when an adhesive is used. More specifically, in the present embodiment, the cover member 151 is disposed in the connection cable 140. Thereafter, the crimping and fixing section 153 is formed, whereby the electric wires 141 of the connection cable 140 are surely fixed to the cover member 151.

In this case, although not shown in the figure, length of the crimping and fixing section 153 is represented as L3. Unlike the present embodiment, for example, it is assumed that an adhesive is applied to the electric wires 141 along the longitudinal axis direction and the electric wires 141 are fixed to the cover member 151 via the outer layer section 143. In this case, although not shown in the figure, application length of the adhesive in the longitudinal axis direction is represented as L4. When the adhesive has fixing strength same as fixing strength of the crimping and fixing section 153, L3 is larger than L4.

Therefore, it is possible to reduce the length of the crimping and fixing section 153 in the longitudinal axis direction in the present embodiment. Therefore, compared with when the adhesive is used, in the present embodiment, the rigid portion is short.

Since the rigid portion is short, mobility of the insertion section 2 is prevented from being deteriorated.

As shown in FIG. 17A and FIG. 18B, since it is unnecessary to fill the adhesive in the inside of the shield member 145, filling work is omitted.

Cleaning treatment for members disposed around the adhesive and drying treatment for drying the adhesive, which are performed when the adhesive is used, are also omitted.

In this way, in the present embodiment, the assembly work involved in reinforcement is only the crimping. Therefore, the assembly work is easily implemented.

By providing the crimping and fixing section 153, the shield member 145 is prevented from expanding in diameter. The proximal end portion of the shield member 145 decreases in diameter. The entire cable fixing mechanism 150 is made compact.

The shield member 145 is connected to the connection cable 140 by the crimping.

As shown in FIG. 17A and FIG. 17B, the proximal-end-side protection member 155 protects the proximal end portion of the cover member 151 including the crimping and fixing section 153 such that the distal end portion of the cover member 151 is exposed from the distal end portion of the proximal-end-side protection member 155. The proximal-end-side protection member 155 has heat shrinkability. Therefore, the inner circumferential surface of the proximal-end-side protection member 155 adheres to the outer circumferential surface of the cover member 151 and the outer circumferential surface of the outer skin 147 of the connection cable 140. Consequently, the proximal-end-side protection member 155 protects the proximal end portion of the cover member 151 and the distal end portion of the connection cable 140. At the same time, the proximal-end-side protection member 155 fixes the cover member 151 to the distal end portion of the connection cable 140 without using an adhesive or the like.

Note that the shrinkage and the fixing may be implemented together with the shrinkage and the fixing by the distal-end-side protection member 159. A shape of a cross section of the proximal-end-side protection member 155 is approximated to a shape of a cross section of the cover member 151 by the shrinkage.

The distal end portions of the electric wires 141 exposed from the distal end portion of the cover member 151 are placed in the groove section 131a provided in the substrate 131. In the thickness direction of the substrate 131, the space section 171 is formed between the cover member 151 and the substrate 131. The distal end portion of the proximal-end-side protection member 155 is placed on the substrate 131 such that the fixing member 157 is disposed between the space section 171 and the bottom surface side of the cover member 151 opposed to the substrate 131 in the thickness direction of the substrate 131.

The distal end portions of the electric wires 141 are fixed to the substrate 131 by, for example, the solder 131b.

As shown in FIG. 17A and FIG. 18A, the fixing member 157 is not disposed in front of the distal end portion of the cover member 151, more specifically, on the distal end portion side of the electric wires 141 exposed from the distal end portion of the cover member 151. The fixing member 157 is not disposed between the proximal-end-side protection member 155 and the substrate 131.

In this way, the fixing member 157 is disposed only in a portion corresponding to the cover member 151 exposed from the proximal-end-side protection member 155. In this state, the fixing member 157 is hardened by, for example, being irradiated with UV light from a side direction of the fixing member 157. The cover member 151 is fixed to the substrate 131 by the hardened fixing member 157. Note that the fixing member 157 may be irradiated with the UV light via the distal-end-side protection member 159.

In order to fix the cover member 151 to the substrate 131, the fixing member 157 prevents a positional shift of the cover member 151 with respect to the substrate 131, prevents a positional shift of the electric wires 141 with respect to the substrate 131, and prevents the cover member 151 from separating from the substrate 131. As a result, the fixing member 157 reinforces the fixing of the distal end portions of the electric wires 141 to the substrate 131. In other words, the fixing member 157 prevents a positional shift of the distal end portions of the electric wires 141, prevents the distal end portions of the electric wires 141 from separating from the substrate 131, and fixes the distal end portions of the electric wires 141 to the substrate 131.

The fixing member 157 quickly hardens when being irradiated with UV light. Therefore, a work time for fixing the cover member 151 to the substrate 131 is reduced.

As shown in FIG. 17A, FIG. 17B, FIG. 18A, and FIG. 18B, the distal-end-side protection member 159 protects the distal end portion side of the connection cable 140 including the entire substrate 131, the distal end portions of the electric wires 141, the cover member 151, and the distal end portion side of the proximal-end-side protection member 155.

The distal-end-side protection member 159 has shrinkability. Therefore, the inner circumferential surface of the distal-end-side protection member 159 adheres to the circumferential surface of the substrate 131, the circumferential surface of the distal end portions of the electric wires 141, the circumferential surface of the cover member 151, and the circumferential surface of the proximal-end-side protection member 155. Consequently, the distal-end-side protection member 159 protects the entire substrate 131, the distal end portions of the electric wires 141, the cover member 151, and the proximal-end-side protection member 155.

At the same time, the distal-end-side protection member 159 fixes the cover member 151 to the substrate 131 and fixes the proximal-end-side protection member 155 to the substrate 131 without using an adhesive or the like. At the same time, the distal-end-side protection member 159 secures strength of the substrate 131.

As shown in FIG. 17A, the distal-end-side protection member 159 has desired length in the axial direction of the distal-end-side protection member 159. More specifically, the distal-end-side protection member 159 is disposed such that the distal end portion of the distal-end-side protection member 159 is located in front of the distal end portions of the electric wires 141 and the proximal end portion of the distal-end-side protection member 159 is located behind the proximal end portion of the substrate 131.

Therefore, the distal-end-side protection member 159 sufficiently prevents the fixing member 157 from leaking out to the outside of the distal-end-side protection member 159.

Like the shield member 145, the distal-end-side protection member 159 electrically protects the substrate 131 and the electric wires 141 such that the noise caused from the electric knife or the like does not electrically affect the substrate 131 or the electric wires 141.

The distal-end-side protection member 159 has insulation properties and secures insulation from not-shown other components disposed around the substrate 131.

In this way, in the present embodiment, with the crimping and fixing section 53, it is possible to reduce a reinforcing section in length and easily implement assembly work involved in reinforcement. In particular, in the present embodiment, as shown in FIG. 17A and FIG. 18B, with the crimping and fixing section 153, it is possible to prevent the electric wires 141 from moving in the longitudinal axis direction or the radial direction of the electric wires 141, prevent the electric wires 141 from being twisted, and prevent the electric wires 141 on the inside of the shield member 145 from shifting in position. As a result, in the present embodiment, with the crimping and fixing section 153, it is possible to fix the electric wires 141 to the shield member 145 and position and fix the electric wires 141 with respect to the cover member 151. In the present embodiment, with the crimping and fixing section 153, it is possible to fix the cover member 151 to the connection cable 140.

In the present embodiment, when the insertion section 2 receives external force, stress is generated in the connection cable 140. Then, the connection cable 140 is about to move in the longitudinal axis direction or the radial direction of the connection cable 140, about to be twisted, and about to extend or shrink with the stress. However, in the present embodiment, the crimping and fixing section 153 is disposed. Therefore, in the present embodiment, with the crimping and fixing section 153, it is possible to prevent the movement, the twisting, and the extension and shrinkage from being transmitted to the distal end portions of the electric wires 141, prevent the positional shift of the distal end portions of the electric wires 141, and fix the distal end portions of the electric wires 141. As a result, in the present embodiment, with the crimping and fixing section 153, it is possible to prevent the distal end portions of the electric wires 141 from separating from the connection substrate, prevent the electric wires 141 from being ruptured or broken, and prevent occurrence of malfunction of the element 133.

In the present embodiment, the crimping and fixing section 153 functions as a rigid portion. However, the crimping and fixing section 153 can more firmly and surely fix the electric wires 141 than when an adhesive is used. As a result, in the present embodiment, it is possible to reduce the rigid portion in length compared with when the adhesive is used.

In the present embodiment, since the rigid portion is short, it is possible to prevent mobility of a movable section 20 such as an insertion section from being deteriorated.

In the present embodiment, since an adhesive does not need to be filled in the inside of the shield member 145, it is possible to omit filling work. In the present embodiment, it is also possible to omit cleaning treatment for members disposed around the adhesive and drying treatment for drying the adhesive, which are performed when the adhesive is used.

In this way, in the present embodiment, it is possible to easily implement, with the crimping, assembly work involved in reinforcement.

In the present embodiment, with the crimping and fixing section 153, it is possible to prevent the shield member 145 from expanding in diameter and reduce the proximal end portion of the shield member 145 in diameter. Therefore, it is possible to make the entire cable fixing mechanism 150 compact.

In the present embodiment, the crimping and fixing section 153 including the constricted section 153a has the length twice or more as large as the diameter of the electric wires 141 in the longitudinal axis direction of the connection cable 140. Therefore, in the present embodiment, it is possible to secure, as desired, fixing length for fixing the electric wires 141 and it is possible to firmly fix the electric wires 141.

In the present embodiment, since the fixing length is secured as desired, even if stress concentrates on a fixing portion (e.g., the proximal end portion of the cover member 151) including the crimping and fixing section 153, it is possible to prevent the fixing portion from being ruptured and it is possible to maintain the fixing.

In the present embodiment, it is possible to increase, with the first adhering section 153c and the second adhering section 153d, an adhesion area and density from a state before the crimping is implemented. Consequently, in the present embodiment, it is possible to prevent the electric wires 141 from moving in the longitudinal axis direction of the electric wires 141 and the radial direction of the electric wires 141, prevent the electric wires 141 from being twisted, and prevent the position of the electric wires 141 on the inside of the shield member 145 from shifting. In the present embodiment, it is possible to surely increase the adhesion area and density with the constricted section 153a. As a result in the present embodiment, it is possible to fix the electric wires 141 with the crimping and fixing section 153.

In the present embodiment, it is possible to fix the cover member 151 to the substrate 131 with the fixing member 157. As a result, it is possible to fix the electric wires 141 with the crimping and fixing section 153. More specifically, in the present embodiment, it is possible to prevent a positional shift of the electric wires 141 with respect to the substrate 131 and it is possible to reinforce the fixing of the distal end portions of the electric wires 141 to the substrate 131.

In the present embodiment, the fixing member 157 quickly hardens when being irradiated with UV light. Therefore, in the present embodiment, it is possible to reduce, with the fixing member 157, a work time for fixing the cover member 151 to the substrate 131.

In the present embodiment, the fixing member 157 is disposed on the inside of the distal-end-side protection member 159. However, the fixing member 157 is not filled in the inside of the distal-end-side protection member 159. In the present embodiment, the fixing member 157 is disposed before the distal-end-side protection member 159 is disposed. Therefore, in the present embodiment, it is possible to make filling work for the fixing member 157 unnecessary and it is possible to easily dispose the fixing member 157.

As shown in FIG. 18A and FIG. 18B, in the present embodiment, the cover member 151 covers the shield member 145. Therefore, in the present embodiment, for example, when a plurality of connection cables 140 are connected to one substrate 131, even if length of the distal end portion of the shield member 145 exposed from the distal end portion of the outer skin 147 is different for each of the connection cables 140, it is possible to make work for aligning the length of the distal end portion of the shield member 145 unnecessary. In other words, in the present embodiment, it is possible to make it unnecessary to take into account fluctuation in the length of the distal end portion of the shield member 145.

In the present embodiment, it is possible to electrically protect the electric wires 141 with the shield member 145 and the cover member 151 such that the noise caused from the electric knife or the like does not electrically affect the electric wires 141.

In the present embodiment, the proximal-end-side protection member 155 has shrinkability. The inner circumferential surface of the proximal-end-side protection member 155 adheres to the outer circumferential surface of the cover member 151 and the outer circumferential surface of the outer skin 147 of the connection cable 140. Consequently, in the present embodiment, with the proximal-end-side protection member 155, it is possible to fix the cover member 151 to the distal end portion of the connection cable 140 without using an adhesive or the like. In other words, in the present embodiment, with the proximal-end-side protection member 155, it is possible to assist the fixing of the cover member 151 fixed to the distal end portion of the connection cable 140 by the crimping and fixing section 153.

In the present embodiment, with the thickness of the proximal-end-side protection member 155, it is possible to separate the distal end portion of the cover member 151, which is exposed from the distal end portion of the proximal-end-side protection member 155, from the substrate 131 by the thickness of the proximal-end-side protection member 155 in the thickness direction of the substrate 131. It is possible to insulate the distal end portion of the cover member 151 from the substrate 131.

In the present embodiment, the distal-end-side protection member 159 has shrinkability. The inner circumferential surface of the distal-end-side protection member 159 adheres to the circumferential surface of the substrate 131, the circumferential surface of the distal end portions of the electric wires 141, the circumferential surface of the cover member 151, and the circumferential surface of the proximal-end-side protection member 155. Consequently, in the present embodiment, with the distal-end-side protection member 159, it is possible to fix the cover member 151 to the substrate 131 and it is possible to fix the proximal-end-side protection member 155 to the substrate 131 without using an adhesive or the like. In other words, in the present embodiment, with the distal-end-side protection member 159, it is possible to assist the fixing of the cover member 151 fixed to the distal end portion of the connection cable 140 by the crimping and fixing section 153 or the proximal-end-side protection member 155.

In the present embodiment, with the distal-end-side protection member 159, it is possible to assist the close attachment of the proximal-end-side protection member 155 closely attached to the distal end portion of the connection cable 140 by heat shrinkage.

In the present embodiment, with the distal-end-side protection member 159, it is possible to assist the fixing of the cover member 151 fixed to the substrate 131 by the fixing member 157.

In the present embodiment, with the distal-end-side protection member 159, it is possible to assist the fixing of the distal end portions of the electric wires 141 fixed to the substrate 131 by the solder 31b.

In the present embodiment, it is possible to secure strength of the substrate 131 with the distal-end-side protection member 159.

In the present embodiment, since the distal-end-side protection member 159 has the desired length, it is possible to sufficiently prevent the fixing member 157 from leaking out to the outside of the distal-end-side protection member 159.

In the present embodiment, with the distal-end-side protection member 159, it is possible to electrically protect the substrate 131 and the electric wires 141 such that the noise caused from the electric knife or the like does not electrically affect the substrate 131 and the electric wires 141.

In the present embodiment, with the distal-end-side protection member 159, it is possible to secure insulation from not-shown other components disposed around the substrate 131.

As explained above, it is possible to reduce the length of the entire cable fixing mechanism 150. It is possible to surely fix the connection cable 140 to the substrate 131 even if the cable fixing mechanism 150 is short.

In the present embodiment, even if stress occurs in the cable fixing mechanism 150 as explained above, it is possible to prevent the cable fixing mechanism 150 from being ruptured. It is possible to easily implement assembly work in the cable fixing mechanism 150.

Note that the apparatus 110 may include a bending unit such as a robot arm other than the endoscope. The cable fixing mechanism 150 may be mounted on the bending unit.

The proximal-end-side protection member 155 may protect the entire cover member 151 in the longitudinal axis direction of the cover member 151. Consequently, it is possible to make the fixing member 157 unnecessary and it is possible to reduce steps of assembly. Naturally, the proximal-end-side protection member 155 may be fixed to the substrate 131 by the fixing member 157.

The crimping and fixing section 153 may be further disposed at the distal end portion of the cover member 151. In this case, for example, the crimping and fixing section 153 is disposed at the distal end of the cover member 151 such that the crimping is not implemented for the distal end portion of the shield member 145 and the distal end portion of the outer skin 147 and the crimping is implemented for only the distal end of the cover member 151 disposed in front of the distal end portion of the shield member 145 and the distal end portion of the outer skin 147.

The crimping and fixing section 153 may be disposed over entire length of the cover member 151. In this way, the crimping and fixing section 153 only has to be disposed in at least a part of the cover member 151.

A crimping direction in forming the crimping and fixing section 153 is not limited to implementation from above the substrate 131 shown in FIG. 18B.

Figure 19A:
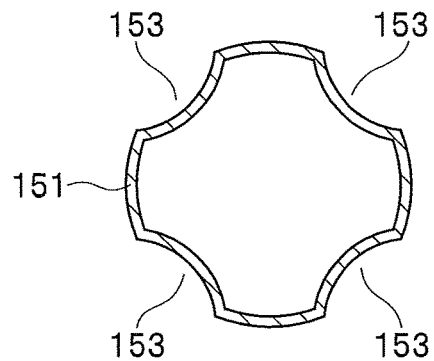
FIG. 19A is a diagram showing another example of a crimping direction in configuring a crimping and fixing section.

That is, the crimping direction may be set in, for example, four directions of an X shape with respect to the cover member 151 shown in FIG. 19A to form the crimping and fixing section 153.

Figure 19B:
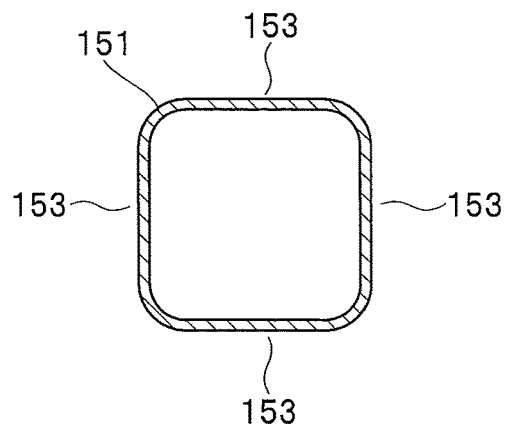
FIG. 19B is a diagram showing another relation between the crimping direction and the crimping and fixing section.

For example, as shown in FIG. 19B, the crimping direction may be set such that the cover member 151 is deformed into a rectangular shape as shown in FIG. 19B.

Figure 19C:
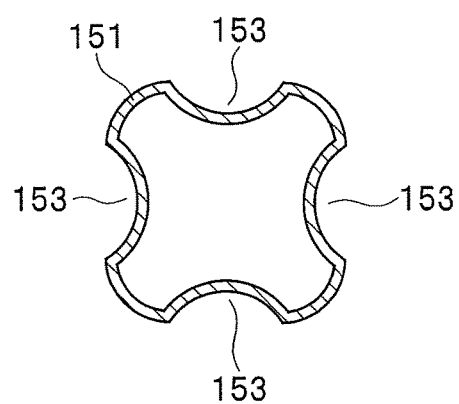
FIG. 19C is a diagram showing another relation between the crimping direction and the crimping and fixing section.

The crimping direction may be set in, for example, four directions of a cross shape with respect to the cover member 151 shown in FIG. 19C to form the crimping and fixing section 153.

Figure 20A:
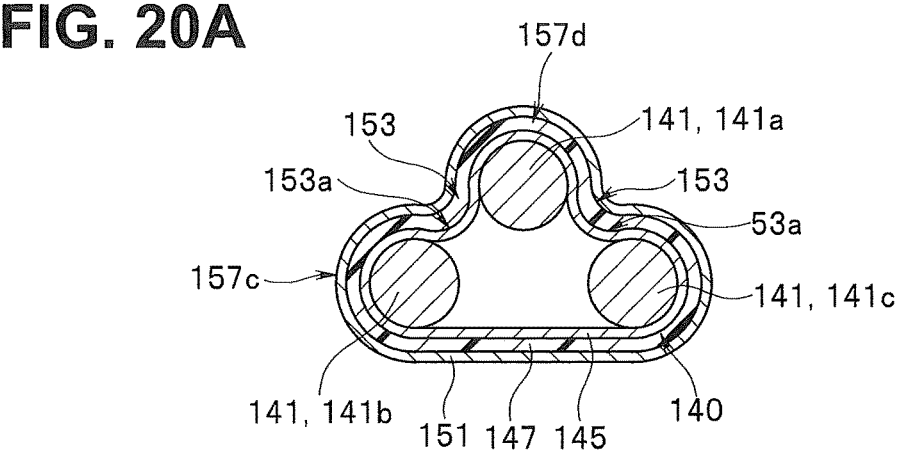
FIG. 20A is a diagram showing still another relation between the crimping direction and the crimping and fixing section.
Figure 20B:
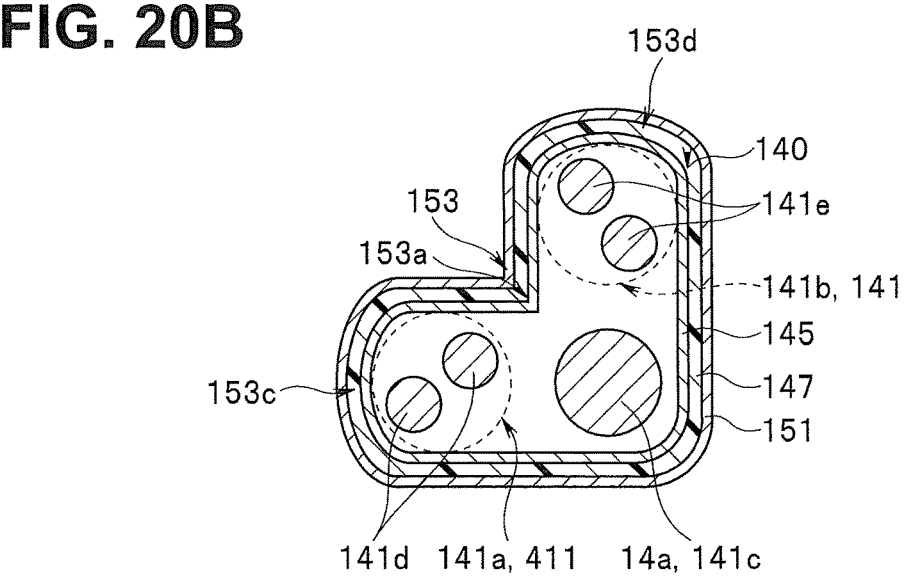
FIG. 20B is a schematic cross sectional view showing an example of crimping in a state in which a connection cable includes, for example, a first core wire bundle section, a second core wire bundle section, and a core wire section.
Figure 20C:
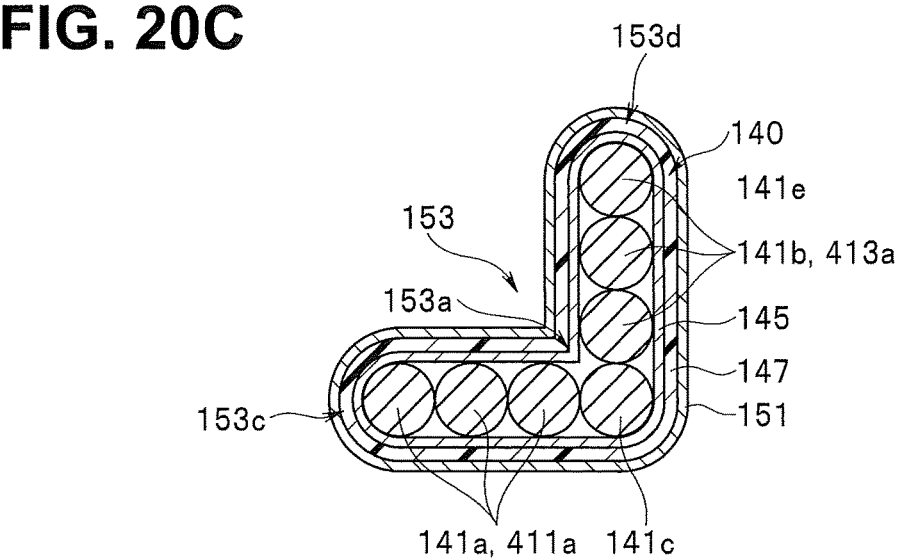
FIG. 20C is a schematic cross sectional view showing an example of crimping in a state in which the connection cable includes, for example, seven element wires.

As shown in FIG. 20A, it is assumed that the connection cable 140 includes, for example, three electric wires 141. In this case, the crimping is implemented such that the cover member 151 is deformed into, for example, a T-shape. In the crimping and fixing section 153, the cover member 151 is crimped by the connection cable 140 such that a part of the cover member 151 penetrates between a first electric wire 141a and a second electric wire 141b, another part of the cover member 151 penetrates between the first electric wire 141a and a third electric wire 141c, and the constricted section 153a is formed by the penetration.

As shown in FIG. 20B, it is assumed that the connection cable 140 includes, for example, three electric wires 141 (the first electric wire 141a, the second electric wire 141b, and the third electric wire 141c). In this state, the first electric wire 141a functions as a first core wire bundle section 411 formed by intertwining, for example, two element wires 141d each other in a spiral shape.

The second electric wire 141b functions as a second core wire bundle section 413 formed by intertwining, for example, two element wires 141e, which are different from the element wires 141d, each other in a spiral shape.

The third electric wire 141c different from the first electric wire 141a functioning as the first core wire bundle section 411 and the second electric wire 141b functioning as the second core wire bundle section 413 has thickness substantially the same as thickness of the first electric wire 141a and the second electric wire 141b.

In this case, the crimping is implemented such that, for example, the cover member 151 is deformed into an L-shape as shown in FIG. 20B. In the crimping and fixing section 153, a part of the cover member 151 penetrates between the first electric wire 141a and the second electric wire 141b. The constricted section 153a is formed by the penetration. The constricted section 153a is disposed between the first electric wire 141a and the second electric wire 141b and crimped by the connection cable 140 to be opposed to the third electric wire 141c.

The first adhering section 153c adheres to substantially a half of an outer circumference of the first electric wire 141a. The second adhering section 153d adheres to substantially a half of an outer circumference of the second electric wire 141b.

As shown in FIG. 20C, it is assumed that the connection cable 140 includes, for example, three electric wires 141. In this state, the connection cable 140 includes the first electric wire 141a functioning as a first group 411a including three element wires and the second electric wire 141b functioning as a second group 413a including three element wires different from the element wires of the first group 411a. In this case, the crimping is implemented such that, for example, the cover member 151 is deformed into an L-shape.

In the crimping and fixing section 153, a part of the cover member 151 penetrates between the first group 411a and the second group 413a. The constricted section 153a is formed by the penetration. The constricted section 153a is disposed between the first group 1411a and the second group 1413a and crimped by the connection cable 140 to be opposed to the third electric wire 141c. The first adhering section 153c closely adheres to substantially a half of an outer circumference of the element wire disposed on an outermost side in the first group 411a. The second adhering section 153d closely adheres to substantially a half of an outer circumference of the element wire disposed on an outermost side in the second group 413a.

In this way, the crimping only has to be implemented for a part of a circumferential surface of the cover member 151. A shape of the proximal end portion of the cover member 151 including the crimping and fixing section 153 is not particularly limited.

The distal end portion of the cover member 151 may be cut obliquely to the longitudinal axis direction of the cover member 151 such that the shield member 145 is viewed.

Figure 21A:
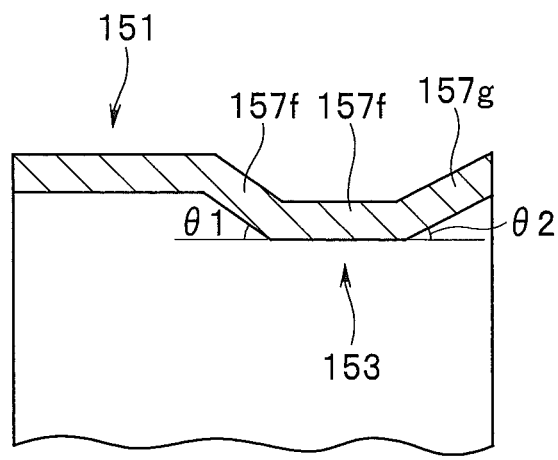
FIG. 21A is a sectional view showing an example of a shape of the crimping and fixing section.

As shown in FIG. 21A, the crimping and fixing section 153 may include a front surface 157f disposed on a front side and a rear surface 157g disposed on a rear side in the longitudinal axis direction of the cover member 151.

The front surface 157f and the rear surface 157g may be skew or may be orthogonal to the longitudinal axis of the cover member 151.

When the front surface 157f and the rear surface 157g are skew, a skew angle $\theta 1$ of the front surface 157f and a skew angle $\theta 2$ of the rear surface 157g may be the same or may be different.

Note that the skew angle $\theta 1$ of the front surface 157f is suitably larger than the skew angle $\theta 2$ of the rear surface 157g. In this case, in the longitudinal axis direction of the cover member 151, a plane section 157h is disposed between the front surface 157f and the rear surface 157g.

Note that it is also possible that the plane section 157h is not disposed and the front surface 157f and the rear surface 157g are directly concatenated. It is also possible that the front surface 157f and the plane section 157h are disposed and the rear surface 157g is not disposed.

Figure 21B:
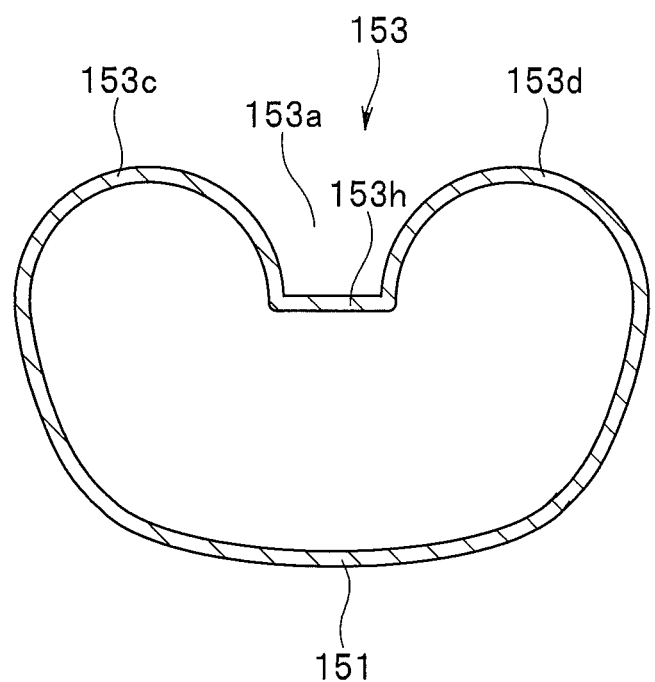
FIG. 21B is a sectional view showing another shape example of the crimping and fixing section.

As shown in FIG. 21B, the cover member 151 may include the plane section 157h formed by the crimping, disposed in a position corresponding to a bottom section of the constricted section 153a, and disposed along the longitudinal axis direction of the cover member 151.

The present invention is not limited to only the embodiment explained above. The present invention can be variously modified and implemented within a range not departing from the spirit of the invention.

What is claimed is:

1. An insertion apparatus comprising:
   a distal end member formed at a distal end portion of an insertion section inserted into a subject, and including a first retaining hole and a second retaining hole;
   a first cylindrical member including a first projecting section whose distal end side is abutted against an abutting surface formed on the distal end member, wherein the first projecting section is exposed to an outer circumference of the distal end member, with the first projecting section abutted against the abutting surface;
   a second cylindrical member including a second projecting section whose distal end side is abutted against the abutting surface formed on the distal end member, the second cylindrical member being different from the first cylindrical member, wherein the second projecting section is exposed to the outer circumference of the distal end member, with the second projecting section abutted against the abutting surface;
   an annular coupling ring that configures a distal end portion of a bendable bending section coupled to the distal end member and includes a contact surface which is brought into contact with proximal end sides of the first projecting section and the second projecting section of the first and second cylindrical members, the coupling ring fixing the first cylindrical member and the second cylindrical member by pinching the first projecting section and the second projecting section between the contact surface and the abutting surface; and a locking member formed by bending a belt-like member;

wherein the first cylindrical member is inserted in the first retaining hole;

the second cylindrical member is inserted in the second retaining hole;

the locking member is disposed on the outer circumference of the distal end member and positions the first cylindrical member and the second cylindrical member with respect to the distal end member in a radial direction of the distal end member; and the coupling ring is fitted on the first cylindrical member, the second cylindrical member, and the locking member, and externally fitted and fixed on the distal end member.

* * * * *